(12) United States Patent
Espevik et al.

(10) Patent No.: US 7,071,310 B1
(45) Date of Patent: Jul. 4, 2006

(54) ANTIBODY AGAINST THE HUMAN TOLL-LIKE RECEPTOR 2 (TLR2) AND USES THEREOF

(75) Inventors: Terje Espevik, Trondheim (NO); Anders Sundan, Trondheim (NO)

(73) Assignee: Leiv Eiriksson Nyskaping AS (NO)

( * ) Notice: Subject to any disclaimer, the term of this patent is extended or adjusted under 35 U.S.C. 154(b) by 194 days.

(21) Appl. No.: 10/130,525

(22) PCT Filed: Nov. 17, 2000

(86) PCT No.: PCT/GB00/04382

§ 371 (c)(1),
(2), (4) Date: May 16, 2002

(87) PCT Pub. No.: WO01/36488

PCT Pub. Date: May 25, 2001

(30) Foreign Application Priority Data

Nov. 18, 1999 (GB) .................................. 9927332

(51) Int. Cl.
- C07K 16/00 (2006.01)
- C07K 16/18 (2006.01)
- C07K 16/24 (2006.01)
- C12P 21/08 (2006.01)

(52) U.S. Cl. .............................. 530/388.1; 530/388.22; 530/388.23; 530/389.1; 530/391.1; 530/391.3

(58) Field of Classification Search ............ 530/388.1, 530/388.22, 388.23, 389.1, 391.1, 391.3
See application file for complete search history.

(56) References Cited

U.S. PATENT DOCUMENTS 5,820,858 A 10/1998 Letureq et al.

FOREIGN PATENT DOCUMENTS

WO WO 98/50547 * 11/1998

OTHER PUBLICATIONS

Aliprantis et al. (1999) Science 285:736-739.
Belisle et al. (1994) Bacteriology 176:2151-2157.
Belvin et al. (1996) Ann. Rev. Cell Dev. Biol. 12:393-416.
Chaudhary et al. (1998) Blood 91:4020-4027.
Chow et al. (1999) J. Biol. Chem. 274:10689-10692.
Faure et al. (2001) J. Immunol. 166:2018-2024.
Fenton et al. (1998) J. Leukoc. Biol. 64:25-32.
Flo et al. (2000) J. Immunol. 164:2064-2069.
Golenbock et al. (1993) J. Biol. Chem. 268:22055-22059.
Heine et al. (1999) J. Immunol. 162:6971-6975.
Hirschfeld et al. (2000) J. Immunol. 165:618-622.
Hoshino et al. (1999) J. Immunol. 162:3749-3752.
Kirschning et al. (1998) J. Exp. Med. 188:2091-2097.
Kuhn et al. (1998) Trends. Microbiol. 6:11-15.
Lemaitre et al. (1996) Cell 86:973-983.
Lemaitre et al. (1997) Proc. Natl. Acad. Sci. 94:14614-14619.
Lien et al. (1998) Blood 92:20842092.
Lien et al. (1999) J. Biol. Chem. 47:33419-33425.
Medzhitov et al. (1997) Nature 388:394-397.
Medzhitov et al. (1998) Molecular Cell 2:253-258.
Muhlradt et al. (1997) J. Exp. Med. 185:1951-1958.
Muzio et al. (1998) J. Exp. Med. 187:2097-2101.
Poltorak et al. (1998) Science 282:2085-2088.
Radolf et al. (1995) J. Immunol. 154:2866-2877.
Rock et al. (1998) Prc. Natl. Acad. Sci. 95:588-593.
Schwandner et al. (1999) J. Biol. Chem. 274:17406-17409.
Sellati et al. (1996) Infect. Immun. 64:3180-7.
Sellati et al. (1999) J. Immunol. 163:2049-2056.
Song et al. (1999) J. Invest. Dermatol. 112:546.
Takeuchi et al. (1999) Gene 231:59-65.
Weis et al. (1994) Infect. Immun. 62:4632-4636.
Williams et al. (1997) EMBO J. 16:6120-6130.
Wright et al. (1990) Science 249:1431-1433.
Yang et al. (1998) Nature 395:284-288.
Yang et al. (1999) J. Immunol. 163:639-643.
Yoshimura et al. (1999) J. Immunol. 163:1-5.
Zhang et al. (1999) J. Biol. Chem. 274:7611-7614.

* cited by examiner

Primary Examiner—Joseph Murphy
Assistant Examiner—Fozia Hamud
(74) Attorney, Agent, or Firm—Dorsey & Whitney LLP

(57) ABSTRACT

The present invention relates to an antibody capable of binding to human TLR2 and which (i) binds only to CD14$^+$ cells in a normal human mononuclear cell population, and not to CD14$^-$ cells; (ii) does not inhibit LPS-induced activation of normal human mononuclear cells, and to the uses thereof, for example in the treatment of bacterial infections which are mediated via the TLR2 receptor, especially bacterial sepsis. In a particular embodiment of this aspects, a utility in the treatment of *Listeria* infections is proposed. The antibodies also have a utility as a general research tool, for example in screening for TLR2 expression, and in the study of TLR2 function. A further aspect of the invention provides use of an agent capable of inhibiting TLR2 activation in the preparation of a composition for the treatment of *Listeria* infections.

24 Claims, 22 Drawing Sheets

Figure 1A:
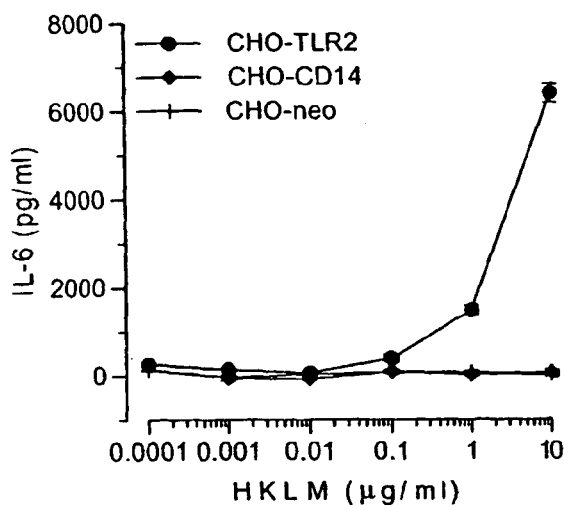

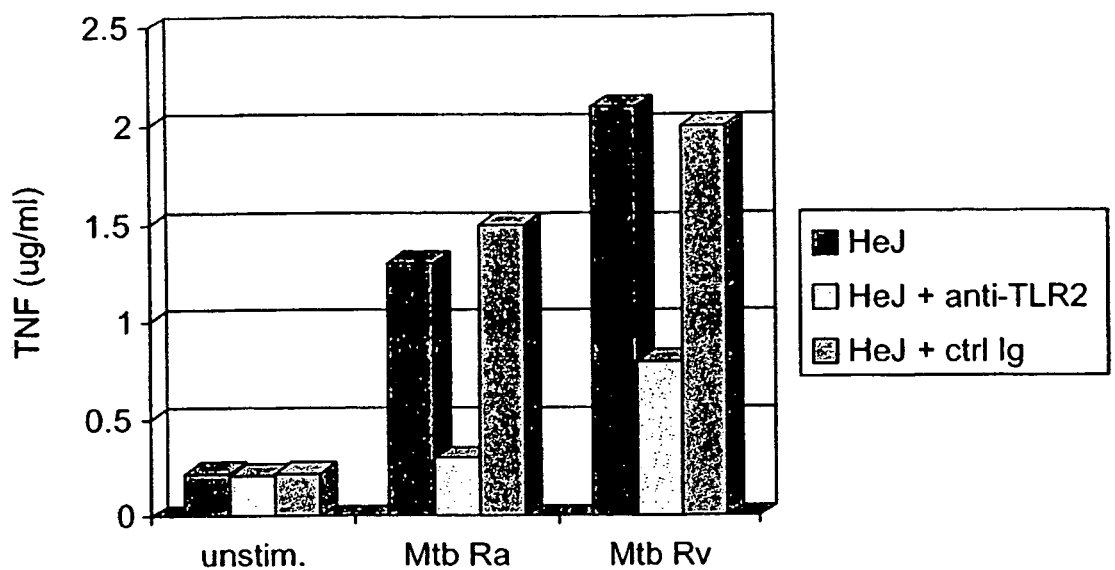
FIG. 14
FIG. 15
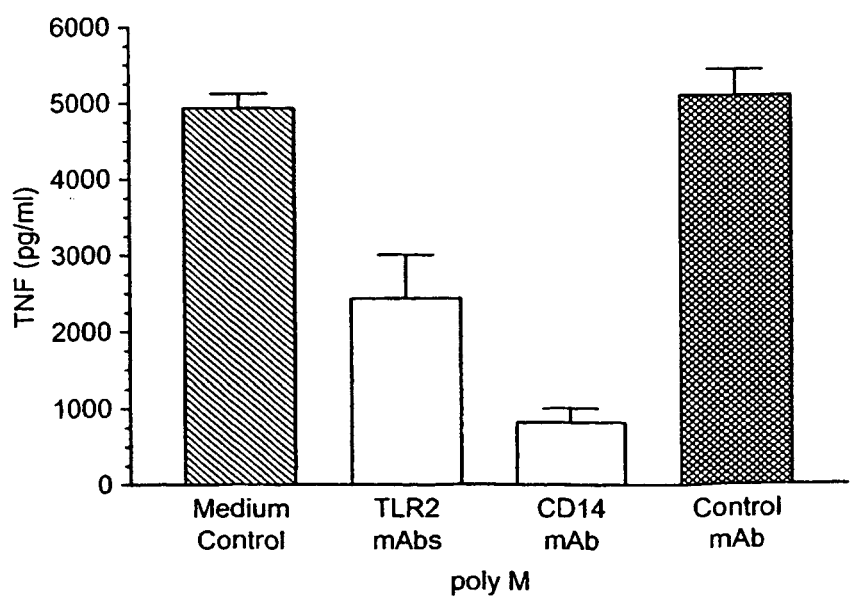

ANTIBODY AGAINST THE HUMAN TOLL-LIKE RECEPTOR 2 (TLR2) AND USES THEREOF

The present invention relates to novel antibodies against the human Toll-like Receptor-2 (TLR2) and to their uses. The antibodies particularly have a therapeutic utility in the treatment of bacterial infections which are mediated via the TLR2 receptor, especially bacterial sepsis. In a particular embodiment of this aspect, a utility in the treatment of *Listeria* infections is proposed. The antibodies also have a utility as a general research tool, for example in screening for TLR2 expression, and in the study of TLR2 function.

The Toll protein was first described as the mediator of dorsal-ventral patterning in *Drosophila* embryos. Subsequently, a family of Toll-like proteins has been identified and ascribed a role in innate immunity in *Drosophila*. For example, the Toll homologue 18-wheeler is responsible for responses to gram negative bacteria, whereas Toll regulates anti-fungal responses (Lemaitre et al., 1996, *Cell* 86:973–983; Lemaitre et al., 1997, *Proc. Natl. Acad. Sci. U.S.A* 94: 14614–14619; Williams et al., 1997, *EMBO J.* 16:6120–6130). In evolutionary terms, these proteins are primordial pattern recognition receptors for animals that totally lack acquired immunity.

Toll is a type I transmembrane receptor that shares homology to components of the Interleukin-1 (IL-1) signalling pathway (Belvin et al., (1996) Annu. Rev. Cell Dev. Biol. 12: 393–416).

Recently, mammalian homologues of Toll have been identified and cloned and designated as "Toll-like receptors" (TLRs), including six human homologues (TLRs 1–6). (Chaudhary et al., (1998), Blood 91, 4020–4027; Rock et al., (1998), Proc. Natl. Acad. Sci. USA, 95, 588–593; Medzhitov et al., (1997), Nature 388, 394–397).

Like *Drosophila* Toll, the TLRs are type I transmembrane proteins with a leucine-rich extracellular domain (LRR) and a cytoplasmic domain with homology to the mammalian IL-1 receptor. Moreover, as for the IL-1R, NFκB and related transcription factors can be activated by mammalian and *Drosophila* Toll receptors through similar signalling cascades (Medzhitov et al., (1997), supra; Medzhitov et al., 1998, *Mol. Cell* 2:253–258).

At least ten such TLR receptors have been identified, but only two of these, TLR2 and TLR4; have been proposed or identified to have any known function. TLR2 and TLR4 have been implicated in cellular responses to lipopolysaccharide (LPS), the major pro-inflammatory constituent of the Gram-negative bacterial outer membrane and have been postulated to act as an LPS signal transducer (Yang et al., (1998), Nature 395, 284–288; Kirschning et al., (1998), J. Exp. Med. 1988, 2091–2097; Poltorak et al., (1998), Science 282, 2085–2088; Yang et al., (1999), J. Immunology 163: 639–543; Song et. al., J. Investigative Dermatology 112' p 546 (1999)).

More recently, TLRs, notably TLR2, have also been implicated in mediating signalling induced by other microbial constituents, including from gram positive bacteria, for example gram positive cell wall components, e.g. peptidoglycans, lipoteichoic acids, and bacterial lipoproteins and lipopeptides (BLPs) (Yoshimura et al., J. Immunology, (1999), 163, 1–5; Aliprantis et al., Science, (1999), 285; 736–738; Brightbill et al., Science, (1999), 285; 732–736).

Some studies have suggested that TLR4 may be the principal signal transducer for LPS (Hoshino et al., 1999, *J.Immunol.* 162:3749–3752). Other studies confirm a role for TLR2 in signal transduction by LPS, but also show activation of TLR2 by a range of other bacterial components from diverse types of bacteria (see e.g.

Yoshimura, supra) suggesting that the true role of TLR2 may lie in the recognition of other bacterial ligands i.e. as a pattern recognition receptor. On the other hand, while TLR2 has the features of a pattern recognition receptor, it is difficult to define a common microbial pattern amongst all of these putative ligands. The list of TLR2 ligands is still not complete, and there is no evidence yet that TLR2 directly binds all these microbial products.

The downstream signalling molecules involved in TLR-mediated cellular activation have not been definitively defined. However, as mentioned above, both TLR2 and TLR4 have a cytoplasmic domain that is homologous to the IL-1 receptor, and it has been proposed that both may activate the NF-KB pathway, and perhaps other pro-inflammatory pathways as well, via their interaction with IL-1 receptor signalling genes, including MyD88, TRAF6, and 1RAK. TLR2 has been shown to interact with CD14 in LPS signalling (see e.g. Yang, 1999 supra) and CD14 co-expression synergistically enhances TLR2-mediated activation (Yang, 1998 and Yoshimura, supra).

The similarities between the signal transduction processes that appear to constitute the inflammatory response to invasion by a variety of bacteria, and the involvement of TLR2, suggests that TLR2 may be very important in the pathogenesis of a wide variety of bacterial infections, most notably sepsis caused by both gram positive and gram negative bacteria. Sepsis is an important, and often fatal, clinical condition. The TLRs, and TLR2 in particular, thus present themselves as important targets for therapeutic intervention in the treatment of bacterial infections known to be mediated by TLR recognition.

TLR2 is thus a physiologically and clinically important molecule. The exact mechanisms involved in TLR2 activation and signalling are not elucidated and accordingly there is a need for further study of this important molecule. There is thus a need for tools to aid in the study of TLR2 expression and function.

The present invention addresses this need by providing an antibody with specificity for the TLR2 receptor. In particular, an antibody is provided which has properties which render it useful not only clinically (e.g. therapeutically), but also as a research tool in the study of TLR2 expression and function.

In one aspect, the present invention thus provides an antibody capable of binding to human TLR2 and which
 (i) binds only to $CD14^+$ cells in a normal human mononuclear cell population, and not to $CD14^-$ cells;
 (ii) does not inhibit LPS-induced activation of normal human mononuclear cells.

By "capable of binding" is meant that the antibody has a binding affinity for human TLR2 (hTLR2) i.e. an immune reactivity to hTLR2.

As will be described in more detail below, antibodies may be obtained which bind specifically to TLR2 and not to other TLRs or to other receptor molecules or cell-surface proteins. An antibody may thus be obtained which binds to TLR2 but not to TLRs of other classes (i.e. other types of TLR, or other members of the TLR family) e.g. TLRS 1, 3–6, and other TLR receptors which have been identified. Antibodies having specificity for (i.e. binding specifically to) TLR2 are preferred according to the present invention.

By "binding specifically" is meant that the antibody is capable of binding to the stated target molecule (i.e. TLR2) in a manner which distinguishes from the binding to non-target molecules. Thus, the antibody either does not bind to non-target molecules, or exhibits negligible or substantially-reduced (as compared to the target) e.g. background, binding to non-target molecules. The antibody thus specifically recognises TLR2.

In particular, we have shown that antibodies may be obtained which bind to TLR2, but do not bind to TLR4 or CD14.

With regard to feature (i) above, as will be described in more detail below, antibodies according to the invention will bind only to CD14⁺ cells within a normal human immune cell population (i.e. cells isolated from a human, and not cell-lines or cells which have been manipulated in any way to express a particular molecule e.g. genetically modified, or activated or stimulated cells), particularly monocytes e.g. peripheral blood mononuclear cells (PBMC). CD14⁻ cells within such a population are not recognised.

As regards feature (ii), antibodies of the invention do not inhibit LPS-induced activation of normal human mononuclear cells, in particular monocytes such as PBMC. As discussed above, LPS is the major pro-inflammatory component of gram negative bacteria and TLR2 has been implicated to play a role in LPS-mediated cell activation and signal transduction. The results presented below, using an antibody according to the present invention, indicate that TLR2 is not the primary or dominant receptor/signal transducer for LPS.

Thus, an antibody of the present invention, when added to a culture or preparation of normal human mononuclear cells which have been stimulated with LPS, will not inhibit parameters of cell activation. In other words, the antibody does not block or reduce the activation of the cell which is induced by the LPS. This is described in more detail in the Examples below.

The term "activation" is used herein, according to its usual meaning in the art, namely the sequence of events triggered by the binding of the effector molecule (in this case LPS) to the cell (i.e. to a cell-surface receptor). These events result in an immune response by the cell to the effector molecule (i.e. the LPS). In particular, according to the present invention, the activation is activation of the TLR2-signalling pathway i.e. the cellular events mediated by activation of TLR2. Such cellular events may be in particular the production and/or release of cytokines or other immune effector molecules, or any other molecule which may play a role in the immune response of the cell e.g. reaction oxygen species (ROS). Such a cellular event may also be a physiological change in the cell itself e.g. the induction of cell death by apoptosis or the cell may become cytotoxic. Activation may also include TLR2-mediated activation of the NFκB pathway. Thus, the TLR2-mediated activation may be associated with NFκB activation. Accordingly, parameters of activation which may be assessed or determined for inhibition or not by the antibodies of the invention include release of cytokines or other molecules, cell death, or activation of other pathways, such as the NF-κB pathway.

Such parameters of activation may readily be assayed using methods known in the art, such as those described in the Examples below (e.g. assays for TNF or IL-6 release, NF-κB translocation, etc.), or those in the prior art, including the references listed above.

In the case of LPS, antibodies of the invention do not inhibit such cellular parameters or indicators of activation as may be seen following stimulation of a normal human mononuclear cell by LPS.

In particular it has been shown that antibodies of the invention do not inhibit LPS-induced TNF release by normal human mononuclear cells.

By "inhibit" is meant a reduction as well as total abrogation of the tested activity or function. Thus, for example, a reduction of 30% or more (e.g. 40%, 50%, 60%, 70%, 80% or 90%, or more) is inhibition according to the present invention. Thus levels of the tested parameter e.g. release of a particular cytokine, may be assessed and compared in the presence and absence of the antibody, following stimulation of the cells e.g. by LPS (or whatever test molecule i.e. stimulant) is being used.

On the other hand, an antibody according to the invention will inhibit lipoprotein or lipopeptide-induced activation of normal human mononuclear cells, in particular bacterial (e.g. gram positive) lipoproteins and lipopeptides, and their synthetic analogues, and especially activation of PBMC induced by the lipopeptides and lipoproteins of *B. Burgdorferi* and *T. pallidum*, and by *Mycobacterium avium*. This is also described in more detail in the Examples below.

An especially preferred feature of an antibody according to the invention is the ability to cross-react with TLR2 molecules of different species. In particular, in a preferred aspect the present invention provides an antibody raised against hTLR2, capable of recognising not only hTLR2, but also TLR2 homologues in other species, most notably murine TLR2 (mTLR2).

As will be described in more detail in the Examples below, an antibody has been obtained, raised in a mouse (i.e. a mouse antibody) against human TLR2, which is able to cross-react with mTLR2. This is a remarkable and unexpected property, since it would not normally be expected for an antibody to cross-react with a molecule deriving from the same species as the immunised host.

This cross-reactivity of a murine anti-hTLR2 antibody with mTLR2 renders the antibody especially useful as a research tool in the study of TLR2 distribution, expression and/or function. Such an antibody may also have utility in purification, and in the inhibition of bacterial infections (e.g. *Listeria* or other gram positive infections—see further below) in mouse animal models.

Thus, in another aspect, the present invention provides a murine antibody capable of binding specifically to hTLR2 and to mTLR2.

In particular, such an antibody according to the invention has been shown to bind to murine macrophages. It has further been shown that the a murine antibody capable of binding specifically to hTLR2 and to mTLR2. antibody can inhibit TLR2-mediated cell activation in murine macrophages, and in particular that the antibody can inhibit cytokine release, in particular TNF release, induced in murine macrophages by bacteria, notably *M. Tuberculosis*.

Whilst the antibody of the invention recognises only CD14⁺ normal human mononuclear cells, it may bind to TLR-2 expressed in artificial cell systems, e.g. cells transfected with a TLR2 encoding gene such as the CHO-TLR2 cells used in the Examples below, or on cell-lines, e.g. human cell lines such as U937 cells.

For example, an antibody according to the invention may have a cell-binding specificity as set out in Table 1 of Example 3 below.

Results presented further in the Examples below, show that mannuronic acid polymers may interact with TLR2 and lead to cell activation, in particular cytokine stimulation. Such polymers may inhibit binding of the antibodies of the invention to human mononuclear cells.

A further advantageous and preferred property of the antibodies of the invention is that they bind specifically to a limited number of cell types in human lymphoid tissue i.e. the antibodies recognise cells in a specific manner in human lymphoid tissue. It may be inferred from this, that the antibody binds to only a limited subset of cells, and these must be TLR2$^+$.

Another advantageous property, which is preferably exhibited by antibodies of the invention, is the inhibition of.

An anti the effect of human alveolar macrophages in killing *Cryptococcus*. body according to the present invention may be prepared using any convenient or desired TLR2 immunogen, for example a natural or synthetic TLR2 protein or polypeptide, e.g. purified isolated TLR2, or an expressed TLR2 protein, which may for example be a fusion protein of TLR2 with another protein or polypeptide. Alternatively, the immunogen may be a part of the TLR2 molecule, for example a domain (e.g. the extracellular domain) or a shorter peptide or polypeptide sequence e.g. an epitopic sequence. Preferably, however the immunogen is one which mimics the natural protein as far as possible. Accordingly, an antibody of the present invention is preferably prepared (i.e. obtainable) using as immunogen a cell expressing functional TLR2 on its surface. Conveniently, such a cell may be a cell which has been genetically engineered (e.g. transfected) to express a functional TLR2 on the surface, e.g. CHO-TLR2 cells as described in the Examples below.

Whilst the antibody of the invention may be of any type, including both polyclonal and monoclonal antibodies, it is advantageous that the antibody is of a single specificity.

Advantageously, the antibody is purified or isolated, especially so as to achieve a single specificity i.e. a single uniform set of binding characteristics i.e. not a mixture of antibodies having varying binding characteristics. Binding specificities can be determined as described above and in the Examples below.

The antibody may be of any convenient or desired species, class or sub-type. Furthermore the antibody may be natural, derivatised or synthetic.

Thus, "antibodies" according to the present invention include:

(a) any of the various classes or sub-classes of immunoglobulin, e.g. IgG, IgA, IgM, IgD or IgE derived from any animal e.g. any of the animals conventionally used, e.g. sheep, rabbits, goats, or mice, or egg yolk.

(b) monoclonal or polyclonal antibodies (c) intact antibodies or fragments of antibodies, monoclonal or polyclonal, the fragments being those which contain the binding region of the antibody, e.g. fragments devoid of the Fc portion (e.g. Fab, Fab', $F(ab')_2$, Fv), the so called "half molecule" fragments obtained by reductive cleavage of the disulphide bonds connecting the heavy chain components in the intact antibody. Fv may be defined as a fragment containing the variable region of the light chain and the variable region of the heavy chain expressed as two chains.

(d) antibodies produced or modified by recombinant DNA or other synthetic techniques, including monoclonal antibodies, fragments of antibodies, "humanised antibodies", chimeric antibodies, or synthetically made or altered antibody-like structures. Also included are functional derivatives or "equivalents" of antibodies e.g. single chain antibodies. A single chain antibody (SCA) may be defined as a genetically engineered molecule containing the variable region of the light chain, the variable region of the heavy chain, linked by a suitable polypeptide linker as a fused single chain molecule.

Methods of making such antibody fragments, and synthetic and derivatised antibodies are well known in the art. Also included are antibody fragments containing the complementarity-determining regions (CDRs) or hypervariable regions of the antibodies. These may be defined as the region comprising the amino acid sequences on the light and heavy chains of an antibody which form the three-dimensional loop structure that contributes to the formation of the antigen binding site. CDRs may be used to generate CDR-grafted antibodies. As used herein, the term "CDR grafted" defines an antibody having an amino acid sequence in which at least parts of one or more sequences in the light and/or variable domains have been replaced by analogous parts of CDR sequences from an antibody having a different binding specificity for a given antigen. One of skill in the art can readily produce such CDR grafted antibodies using methods well known in the art (see Borrebaeck, Antibody Engineering: A Practical Guide, W.H. Freeman and Company, New York, 1992).

A chimeric antibody of the present invention may be prepared by combining the variable region of an anti-TLR2 antibody of one species according to the present invention with the constant regions of an antibody derived from a different species. A chimeric antibody may be constructed, for example, according to methods described by Shaw et al., in J. Immun. 1987, 138: 4534 and Sun et al., in PNAS USA, 1987, 84: 214–218.

Monoclonal antibodies and their fragments and derivatives, are preferred antibodies according to the present invention. A further aspect of the invention is thus a hybridoma or cell-line producing an antibody of the invention as defined above.

In particular, a monoclonal antibody has been obtained, having the particular properties and characteristics (e.g. binding and inhibition characteristics) set out and defined above. This antibody is described herein as MAb TL2.1, and its production is described in Example 1 below. The hybridoma producing this antibody was deposited under the terms of the Budapest Treaty at the European Collection of Cell Cultures (ECACC), Centre for Applied Microbiology and Research, Salisbury, Wiltshire SP4 OJG, United Kingdom on 28 Oct. 1999 under the Accession No. 99102832.

Accordingly, a preferred embodiment of this invention provides a monoclonal antibody (identified as TL2.1) produced by (or obtainable from) the hybridoma cell line of ECACC deposit Accession No. 99102832.

In a further related aspect, the invention provides a hybridoma (or hybrid cell line) being that on deposit at the ECACC under Accession No. 99102832.

Also part of the invention are antibodies and hybridomas or cell lines having the identifying characteristics of antibody TL2.1 and the hybridoma of ECACC Accession No. 99102832.

By "identifying characteristics" is meant, for example, the properties and characteristics e.g. functional effects (e.g. inhibitory effects) discussed above for antibodies of the invention, and in the Examples below. In particular, included under this aspect of the invention are antibodies having the same binding specificities and/or binding properties as Mab TL2.1 and hybridoma ECACC Accession No. 99102832.

Thus, for example, the genes encoding antibody TL2.1 may be identified, cloned and examined. These may be utilised to create an antibody construct (e.g. a synthetic antibody chain, a CDR grafted antibody or a chimeric antibody) having a binding pattern and/or specificity identical to that of antibody TL2.1.

The specificity of antibody TL2.1 has been examined and is described in the Examples below. Thus, the antibody has been shown to have specificity for TLR2, as demonstrated by binding data showing binding to TLR2-expressing cells, using flow cytometry, and also by immunoprecipitation of lysates of cells expressing TLR2. In particular, antibody TL2.1 can immunoprecipitate a protein of approximately 98 kD molecular weight (as determined by SDS-PAGE on an 8% non-reducing gel) from a lysate of a cell expressing a TLR2-Flag fusion tag construct.

An antibody of the invention can be obtained or made according to techniques standard and well known in the art and widely described in the literature. Thus, a host animal may be immunised with a selected immunogen as described above, and used to generate a polyclonal antibody, or more preferably, a monoclonal antibody using well known standard techniques, for example as described in Example 1. Likewise techniques for generating fragments of antibodies or antibody derivatives are also well known in the art. Thus, for example phage display methods may be used to make antibodies as described in Winter et al., Annu. Rev. Immunol. 1994, 12: 433–55.

The antibodies of the invention can be used in a wide variety of applications, including therapeutic, diagnostic, analytical and research applications.

From the research point of view, the antibodies are, of course, very useful tools in the study of TLR2 expression and function, and may be used to help explore and study the various mechanisms and processes involved in TLR2 activation and signal transduction. The antibodies can also be used in physiological studies of immune cells. Further uses include the study of tissue expression of TLR2 and in assays of TLR2, for example for assays of soluble TLR2, e.g. in biological fluids.

Therapeutically, the antibodies have a utility in the treatment of microbial infections which are mediated by binding to TLR2 or otherwise associated with TLR2 expression and function.

Intervention at the level of the TLR2 receptor has been proposed in the treatment of LPS-induced septic shock (Yang, 1991, supra) i.e. in the treatment of gram negative sepsis-causing bacterial infections. We propose also that such intervention may be useful in the treatment of gram positive septic shock and other gram positive infections.

Thus, a further aspect of the present invention provides an antibody according to the invention as defined above for use in therapy or diagnosis, and in particular for use in the treatment of bacterial infections, both gram-positive and gram negative, especially infections by sepsis-causing bacteria (e.g. in the treatment of sepsis or septic shock). Both chronic and acute bacterial infections are included.

Alternatively viewed, this aspect of the invention provides use of an antibody according to the invention as defined above for the preparation of a composition for use in the treatment of bacterial infections.

Yet another aspect provides a method of treatment of a bacterial infection in a patient, said method comprising administering to said patient an antibody according to the invention as defined above.

The term "treatment" is used herein broadly to include both therapeutic and prophylactic treatment i.e. both therapy and prevention.

The antibodies of the invention may be administered to patients in order to block or inhibit TLR2 activation by the infecting or invading bacteria and thereby preventing or reducing the cascade of events triggered by TLR2 activation, which lead ultimately to septic shock or other manifestations of bacterial infection.

The antibodies may be formulated for administration in any convenient manner according to principles and methods well known in the art and described in the literature.

A still further aspect of the present invention thus provides a pharmaceutical composition comprising an antibody according to the invention as defined above, together with at least one pharmaceutically acceptable carrier or diluent.

A pharmaceutically acceptable carrier may be any compatible, non-toxic substance suitable to deliver the antibodies to the patient. Sterile water, buffers, salines, alcohol, emulsions, fats, waxes and inert solids may for example be used as the carrier or any other carrier known in the art. Other pharmaceutically acceptable formulation aids e.g. buffering agents, dispersing agents, wetting agents etc. may also be included.

The antibodies and pharmaceutical composition of this invention may be administered in any convenient or desired manner, for example by oral or parenteral administration. Conveniently, the pharmaceutical compositions may be administered parenterally, i.e., subcutaneously, intramuscularly or intravenously. For such administration the carrier is preferably an aqueous carrier. A variety of aqueous carriers can be used, e.g. water, buffered water, 0.4% saline, 0.3% glycine and the like. These solutions are sterile and generally free of particulate matter. These compositions may be sterilised by conventional, well known sterilisation techniques. The compositions may contain pharmaceutically acceptable auxiliary substances as required to approximate physiological conditions such as pH adjusting and buffering agents, tonicity adjusting agents and the like, for example sodium acetate, sodium chloride, potassium chloride, calcium chloride, sodium lactate, etc. The concentration of antibody in these formulations can vary widely, i.e. from less than 0.5%, usually 1% to as much as 15 or 20% by weight and will be selected primarily based on fluid volumes, viscosities, etc., preferably for the particular mode of administration selected.

Thus, a typical pharmaceutical composition for intramuscular injection could be made up to contain 1 ml sterile buffered water and 50 mg of antibody. A typical composition for intravenous infusion could be made up to contain 250 ml of sterile Ringer's solution and 150 mg of antibody. Actual methods for preparing parenterally administrable compositions will be known or apparent to those skilled in the art and are described in more detail in, for example *Remington's Pharmaceutical Science,* 15th Ed., Mack Publishing Company, Easton Pa. (1975).

The antibodies of this invention can be lyophilised for storage and reconstituted in a suitable carrier prior to use. Art-known lyophilisation and reconstitution techniques can be employed. It will be appreciated by those skilled in the art that lyophilisation and reconstitution can lead to varying degrees of antibody activity loss (e.g. with conventional immune globulins, IgM antibodies tend to have greater activity loss than IgG antibodies) and that use levels may have to be adjusted to compensate.

The compositions containing the antibody of the invention can be administered for the prophylactic and/or therapeutic treatment of gram-negative or gram positive bacterial disease. In therapeutic application, compositions are administered to a patient already infected with the bacteria, in an amount sufficient to cure or at least partially arrest the infection and its complications. An amount adequate to accomplish this is defined as a "therapeutically effective dose". Amounts effective for this use will depend upon the severity of the infection and the general state of the patient's own immune system but generally range from about 0.25 to about 200 mg of antibody per kilogram of body weight, e.g. 0.5 or 1 to 50 mg/kg body weight with dosages of from 5 to 25 mg per kilogram being more commonly used.

In prophylactic applications, compositions containing the antibody may be administered to a patient not already infected by the bacteria, to enhance the patient's resistance to such potential infection. Such an amount is defined to be a "prophylactically effective dose". In this use, the precise amounts again depend upon the patient's state of health and general level of immunity, but generally range from 0.1 to 25 mg per kilogram, especially 0.5 to 2.5 mg per kilogram.

Single or multiple administrations of the compositions can be carried out with dose levels and pattern being selected by the treating physician.

The antibodies may also be administered in combination, together, separately, sequentially or simultaneously, with other pharmaceutical agents active against bacterial infections, e.g. antibiotics or other anti-bacterial agents.

The antibodies of the invention further have a utility in assays for the TLR2 receptor. These may, for example, be assays to detect the presence or amount of the receptor, or to detect or monitor its expression, or even to assess TLR2 function. The assays may thus be qualitative, quantitative or semi-quantitative and include assays for soluble TLR2 receptor, (i.e. not cell-surface bound). The sample for assay may be any sample containing TLR2 e.g. a cell culture or preparation, a cell lysate, a biological or clinical sample, or any laboratory sample which may contain a TLR2 protein.

Such assays may, for example, simply involve contacting a sample containing TLR2, or a cell or culture (which may or may not express TLR2), with the antibody, and detecting whether or not it binds. Such an assay may be carried out using any of the well known immunoassay techniques which are widespread in the art and described in the literature, e.g. sandwich assays, competitive assays, immunometric assays etc. Other assay formats may also be used, e.g. assays based on flow cytometry. The antibody may be labelled, for example, and binding to TLR2 (or to cells expressing TLR2) may be detected and/or measured by means of the label. Labelling may be by any convenient or desired means and a wide variety of labels and labelling techniques for antibodies and proteins are well known in the art and widely described in the literature.

Such labels may include for example fluorochromes, radioisotopes, coloured dyes or other chromogenic agents, enzymes, colloidal metals, chemi- and bio-luminescent compounds. The labels may be directly detectable, or signal-giving, such as those listed above, or they may be labels which take part in a signal-giving or detectable reaction, for example by binding to another molecule e.g. they may be an indirectly detectable label. Thus, a label may be a small molecule such as a hapten, or a tag, e.g. biotin, which may be bound by a binding partner therefor (e.g. streptavidin/avidin for biotin). A further aspect of the invention thus provides a labelled antibody as defined above, i.e. an antibody as defined above carrying or provided with a label.

For use in assays, the antibodies can be bound to various carriers or immobilised on a solid support. Examples include glass, polystyrene, polyethylene etc., dextran, nylon, amyloses, celluloses, polyacrylamides, agaroses or solid surfaces such as particles, e.g. magnetic or non-magnetic beads, the surfaces of plates, wells, and tubes, or strips etc. Methods for coupling or immobilising antibodies or proteins are well known in the art.

Accordingly, a still further aspect of the invention provides a method of detecting TLR2 in a sample which comprises contacting said sample with an antibody as defined above, and determining whether there is binding to the sample.

Such assays may have utility in an analytical or research setting. They may also have a clinical utility, for example in diagnosis of bacterial infections, or in monitoring TLR2 expression by immune cells from patients who may be susceptible to infections.

As described in detail in Example 1 below, our results have shown that TLR2 may signal cell activation by *Listeria* sp., particularly *Listeria monocytogenes*. *Listeria* is the causative agent of food-borne listeriosis, a serious infection, which although rare, is potentially life-threatening and may have serious consequences. The need for effective treatments against *Listeria* infections is thus significant.

A particularly important aspect of the present invention therefore, lies in the use of the antibodies in the treatment of *Listeria* infections.

More broadly viewed, this aspect of the invention also provides the use of an agent capable of inhibiting TLR2 activation in the preparation of a composition for the treatment of *Listeria* infections.

In addition to the antibodies of the invention, or other anti-TLR2 antibodies, such an agent may be any agent which acts either by blocking the TLR2 receptor, to prevent or reduce binding of *Listeria* or listerial components, or which otherwise interferes in (e.g. inhibits) the signalling pathway of TLR2 activation.

The latter group of agents may include inhibitors of NF-κB activation, which may include, for example, anti-inflammatory drugs e.g. aspirin, sodium salicylate, and glucocorticoids, or inhibitors of IL-1 signalling e.g., IL-1 receptor antagonists.

The formulation and administration of such an agent may be along the lines discussed for the antibodies above.

Figure 1B:
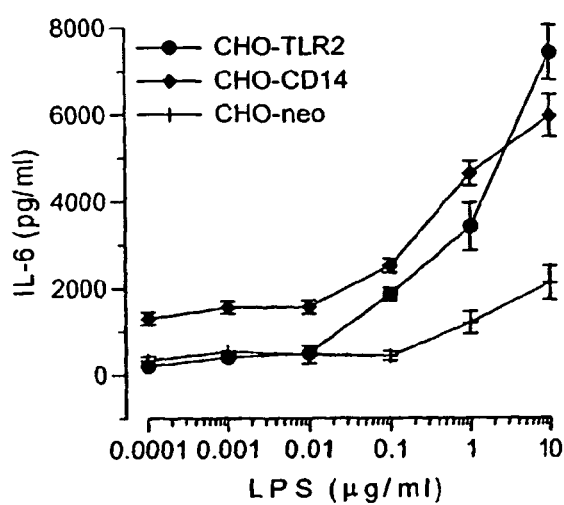
Figure 1C:
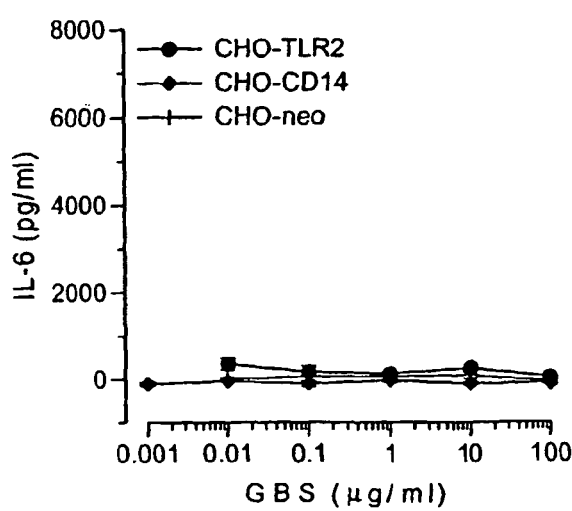

The invention will now be described in more detail in the following non-limiting Examples, with reference to the drawings, in which:

FIG. 1 is a set of graphs A, B, C showing that heat killed *Listeria monocytogenes* (HKLM) induce IL-6 production from CHO-TLR2, but not from CHO-CD14 cells. CHO-TLR2, CHO-CD14 and CHO-neo cells were incubated with increasing concentrations of HKLM (A), LPS (Lipopolysaccharide) (B) or GBS (C) for 14 h. Supernatants were collected and assayed for IL-6 bioactivity. Background levels of IL-6 for each cell transfectant are subtracted from the data presented. The graphs show IL-6 (pG/ml) against concentration of bacteria or LPS µg/ml). One representative of four experiments is shown (mean±SD of triplicate wells).

FIG. 2 is a set of graphs showing that HKLM, but not group B *Streptococcus* Type III (GBS), induce NFκB-translocation in CHO-TLR2 cells. (A) CHO-TLR2 and CHO-neo cells were exposed to increasing concentrations of HKLM, LPS or GBS for 1 h before nuclear extracts were prepared and analyzed for NFκB translocation by a PhosphoImager system. The intensity of the bands was quantified, and results are presented as relative units. (B) CHO-TLR2 cells were stimulated with 1 µg/ml HKLM, 0.1 µg/ml LPS or 100 µg/ml GBS for the indicated periods of time before NFκB-activity was measured. The graphs show NFκB (relative units) against (A) concentration of bacteria or LPS (µg/ml) and (B) cell stimulation time (minutes).

FIG. 3 shows binding of the TLR2 mAb, TL2.1, to CHO-transfectants and PBMC. Prior to FACScan analysis, CHO-transfectants CHO-TLR2 (Ai), CHO-neo (Aii), CHO- TLR4 A(iii) and CHO-CD14 A(iv) or human PBMC (Bi, ii & iii) were stained with TLR2 mAb (TL2.1), FLAG mAb or CD14 mAb as described in Example 1. In (A), results are shown as linear-log scale histograms, but in (B) the data are two-channel log—log scale dot histograms as PBMC were stained with a CD14 mAb (Bi), the TLR2 mAb (Bii), or with both B(iii). The percentage of total cells in each quadrant is indicated in Figures B(i, ii & iii). Similar data were obtained in two independent experiments.

Figure 4:
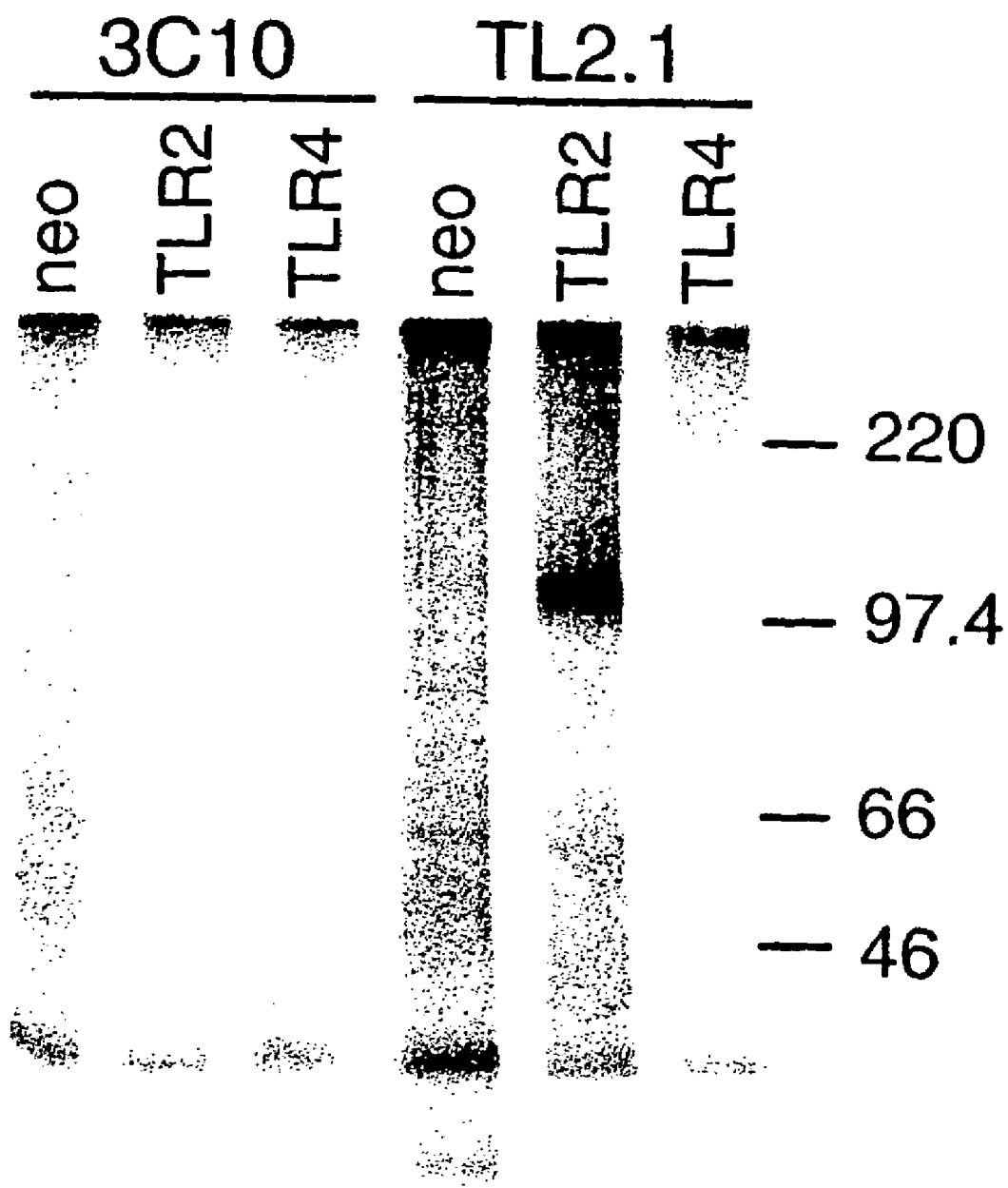

FIG. 4 shows immunoprecipitation of TLR2 with TL2.1. Lysates from $^{35}$S-labelled CHO-TLR2, CHO-neo and CHO-TLR4 cells were immunoprecipitated with TL2.1 or a CD14 mAb (3C10) attached to Sepharose anti-mouse IgG. The precipitates were subjected to 8% SDS-PAGE and analyzed by autoradiography. Bands from the Mw-marker (in kDa) are indicated, and the lanes are labelled with the type of cell-lysate. The gel from one of two similar experiments is shown.

Figure 5A:
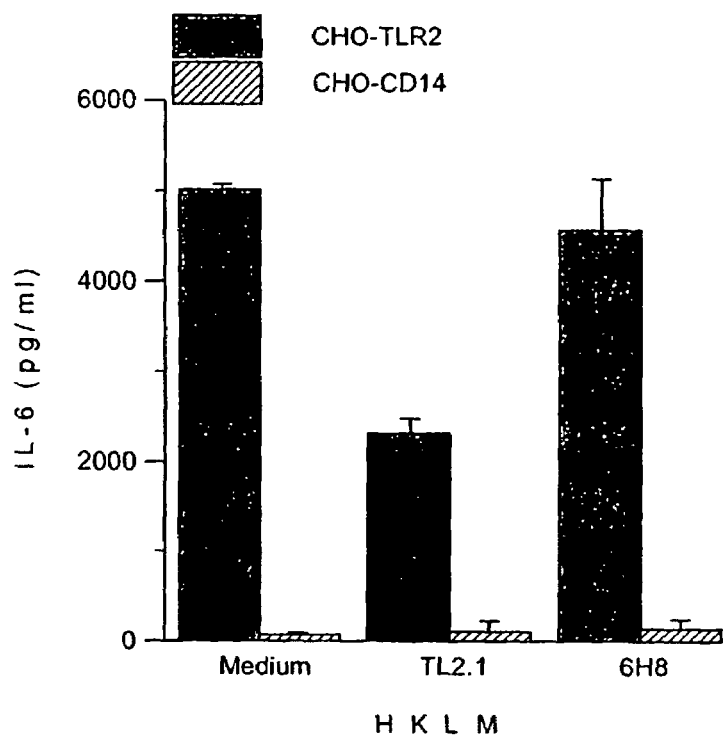
Figure 5B:
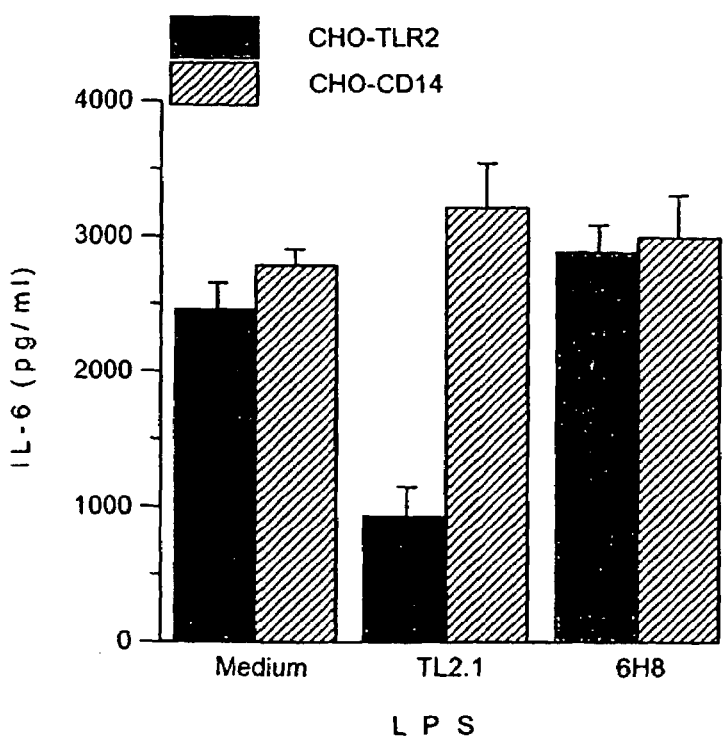

FIG. 5 consists of two graphs showing that TL2.1 inhibits HKLM- and LPS-induced IL-6 production from CHO-TLR2 cells. CHO-TLR2 and CHO-CD14 cells were pretreated with 10 μg/ml of either TL2.1 or a control mAb, 6H8, for 30 min at RT, prior to addition of HKLM (10 μg/ml —FIG. 5a) or LPS (10 μg/ml —FIG. 5b). The cells were incubated for additional 14 h at 37° C. before bioactive IL-6 in supernatants was assayed. In each graph, one representative of three experiments is shown (mean±SD of triplicate IL-6 measurements). The graphs show concentration of IL-6 (pg/ml) against each antibody.

Figure 6A:
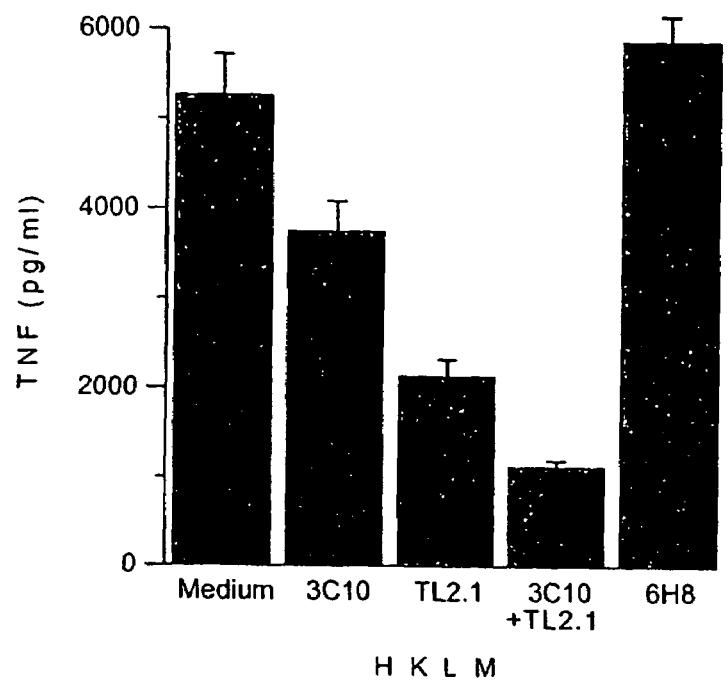
Figure 6B:
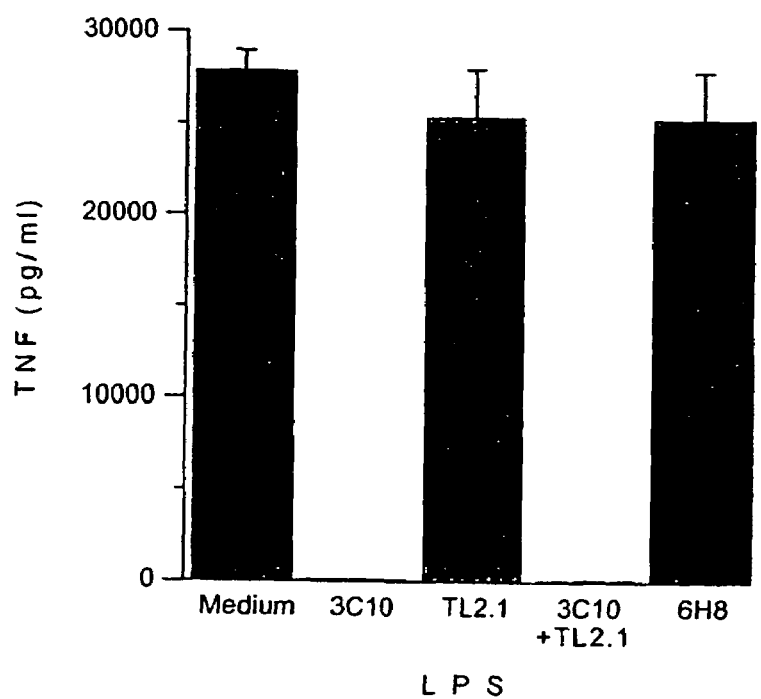

FIG. 6 shows that TLR2 and CD14 are both involved in HKLM-induced TNF-production from human monocytes. Human monocytes were pretreated with 10 μg/ml of either 3C10 (anti-CD14), TL2.1 (anti-TLR2), 3C10 and TL2.1, or 6H8 (control mAb) for 30 min, RT, at serum free conditions. HKLM (200 ng/ml—FIG. 6a)) or LPS (1 ng/ml—FIG. 6b) was added, and the cells incubated for additional 8 h at 37° C. before supernatants were collected and assayed for TNF bioactivity. The results from a representative experiment are shown by plotting TNG (pg/ml) against each antibody (mean±SD of triplicate wells), and similar data were obtained in three independent experiments.

Figure 7A:
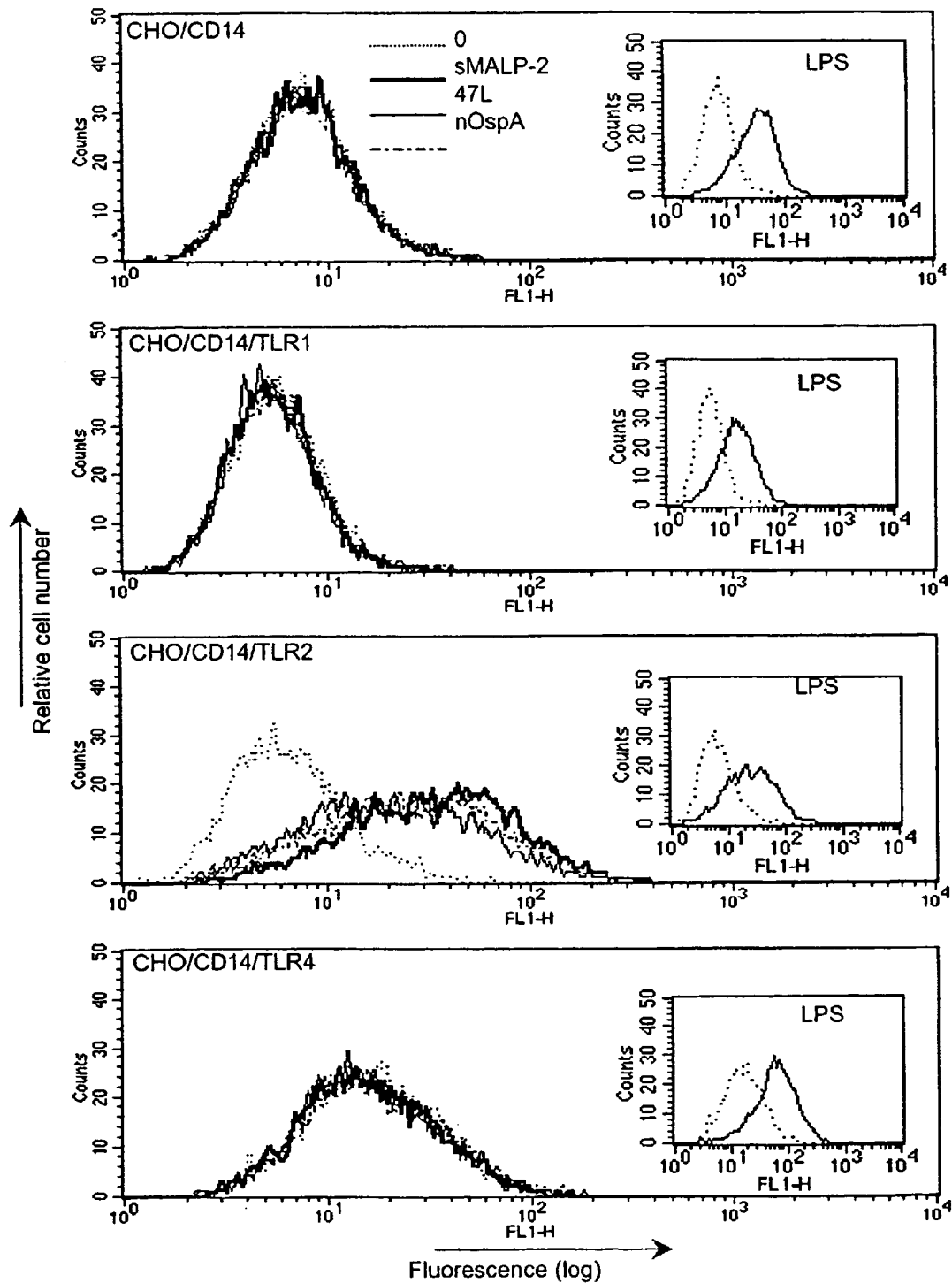
Figure 7B:
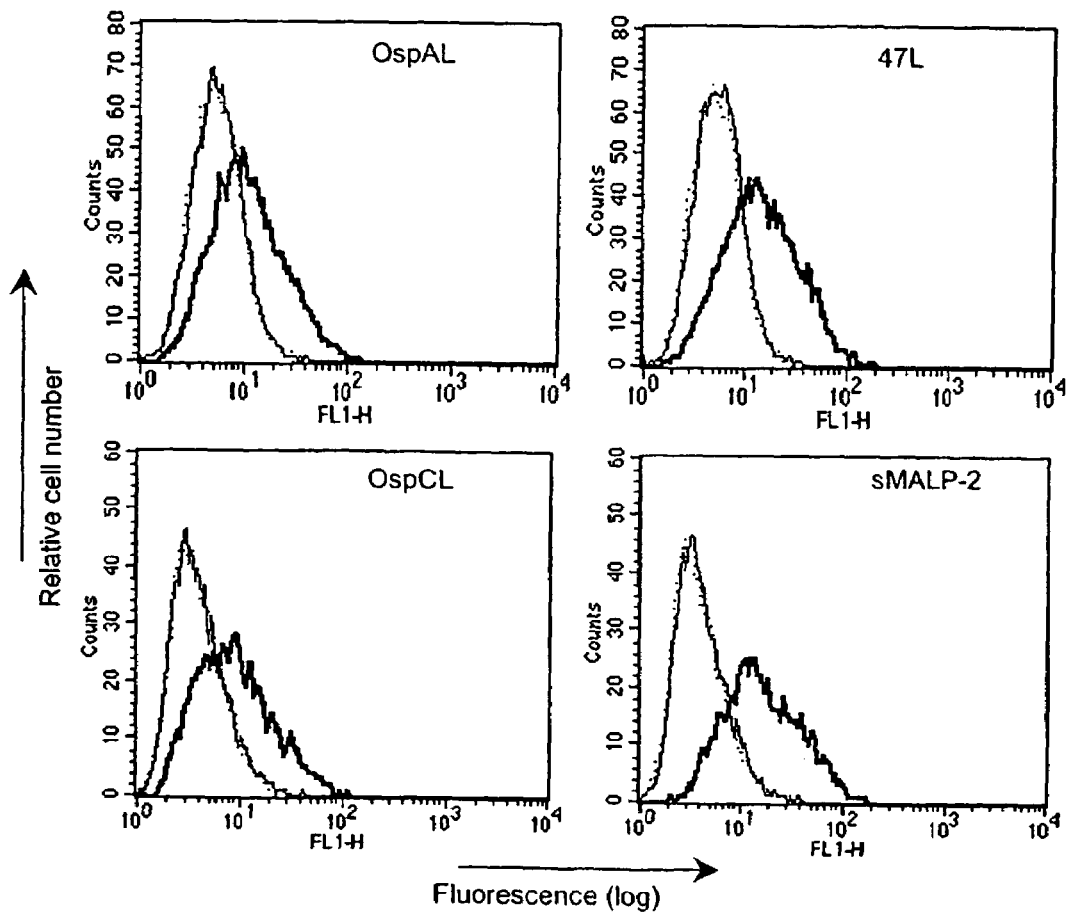
Figure 8A:
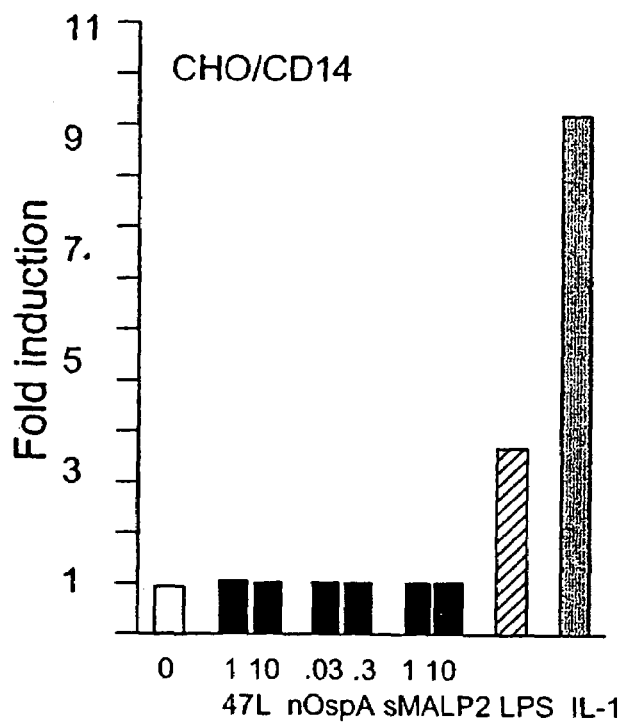
Figure 8B:
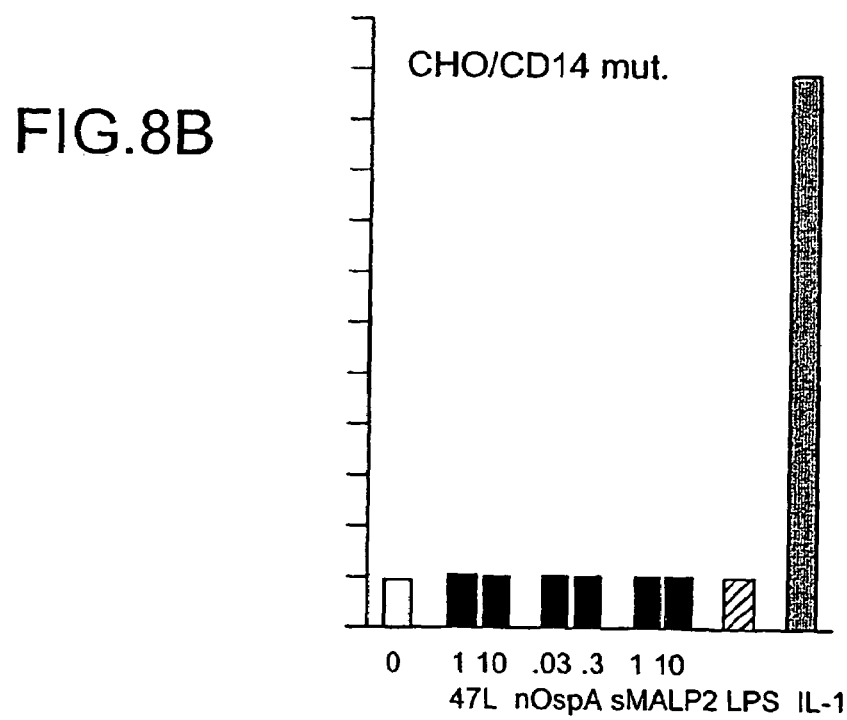
Figure 8C:
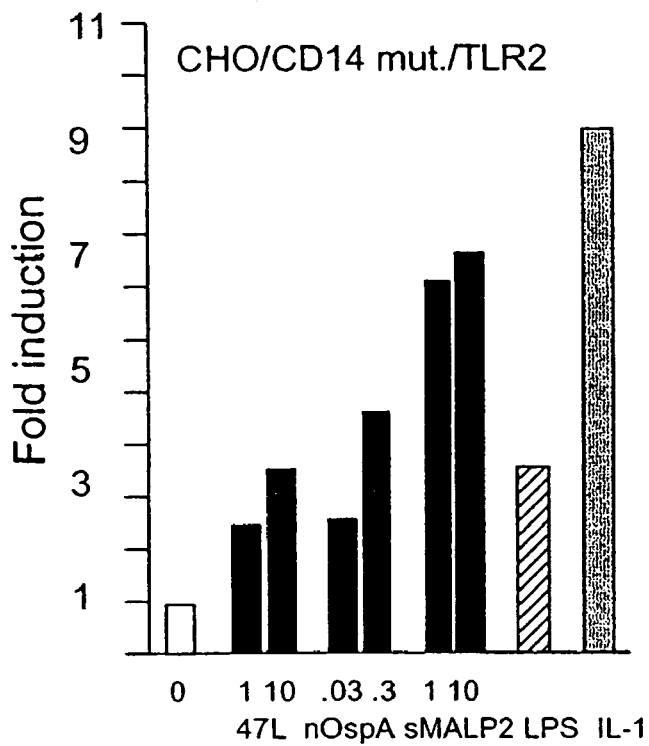
Figure 8D:
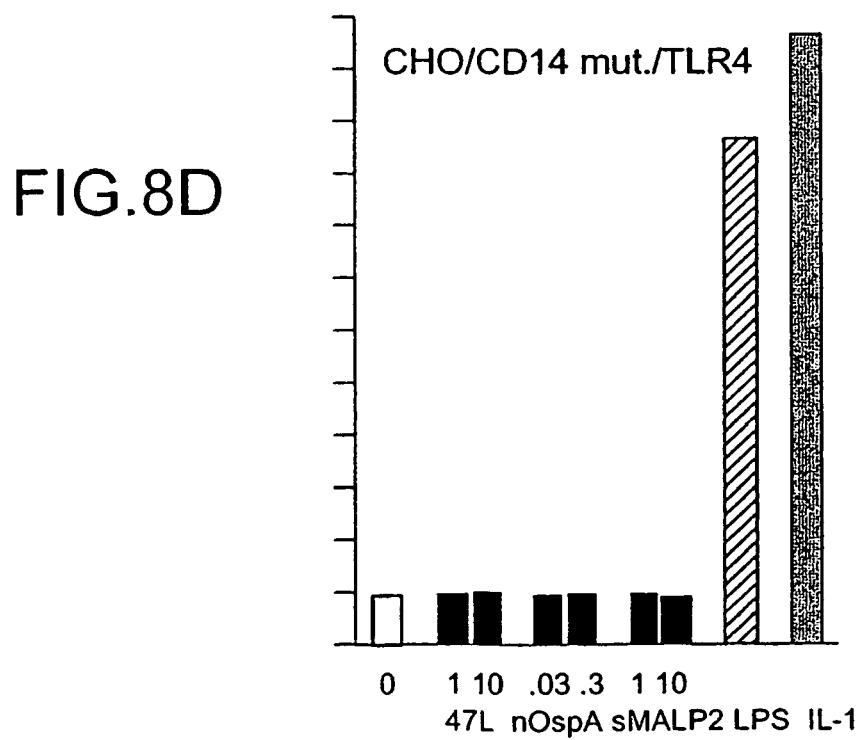

FIG. 7 is a set of graphs showing that expression of TLR2 in CHO cells confers responsiveness to B. burgdorferi natural lipoprotein nOspA, T. pallidum synthetic lipopeptide 47L and M. fermentans synthetic lipopeptide sMALP-2. In FIG. 7A) CHO/CD14, CHO/CD14/TLR1, CHO/CD14/TLR2 and CHO/CD14/TLR4 reporter cells were incubated with medium alone (dotted lines), B. burgdorferi nOspA (stippled lines, 300 ng/ml), T. pallidum 47L (thin lines, 10 μg/ml), M. fermentans sMALP-2 (thick lines, 25 nM) and LPS (inserts, thin lines, 100 ng/ml) for 20 hours. Activation of NF-κB was measured by the appearance of reporter transgene (surface CD25) by flow cytometry. Relative cell number (counts) is given on the y-axis and fluorescence (long-scale) FL1-H on the x-axis. Dotted lines represent unstimulated cells. In FIG. 7B) The CHO/CD14/TLR2 reporter cell line was exposed to 3.4 μM of synthetic lipopeptides OspAL and 47L, 6.8 μM of OspCL and 100 nM of sMALP-2 or similar amounts of the corresponding unlipidated hexapeptides as described in FIG. 7A. Cells stimulated with lipopeptides are indicated by the thick lines; the corresponding unlipidated peptides are represented by thin lines, and unstimulated cells by dotted lines. Relative cell number (counts) is given on the y-axis and fluorescence (long-scale) on the x-axis. Dotted lines represent unstimulated cells. Shown is one representative experiment out of four performed.

FIG. 8 is a set of graphs showing that transfection of a mutant LPS non-responder CHO/CD14 cell line with TLR2, but not TLR4, renders the cells responsive to bacterial lipoproteins and lipopeptides. LPS non-responder mutant CHO/CD14 cells [CHO/CD14 mut. were transfected with TLR2 (FIG. 8C) or TLR4 (FIG. 8D). Clonal derivatives were analyzed in comparison to LPS responsive CHO/CD14 cells (FIG. 8A), and the untransfected mutant cell line (FIG. 8B) and fold induction is shown on the Y axis of each graph as a measure of the responses (activation) to IL-1 (gray bars), LPS (hatched bars) or lipoprotein/lipopeptides (dark bars). "0" signifies no treatment (open bars); concentrations for 47L and nOspA are given in μg of ligand per ml; sMALP-2 in nM, LPS was used at 100 ng/ml and IL-1 was at 1 ng/ml. Cells were stimulated for 20 hours. The cells were then stained for reporter transgene expression and analyzed by flow cytometry. Activation is expressed as the fold induction of median channel fluorescence in comparison to unstimulated cells. One representative out of two experiments performed is shown.

Figure 9A:
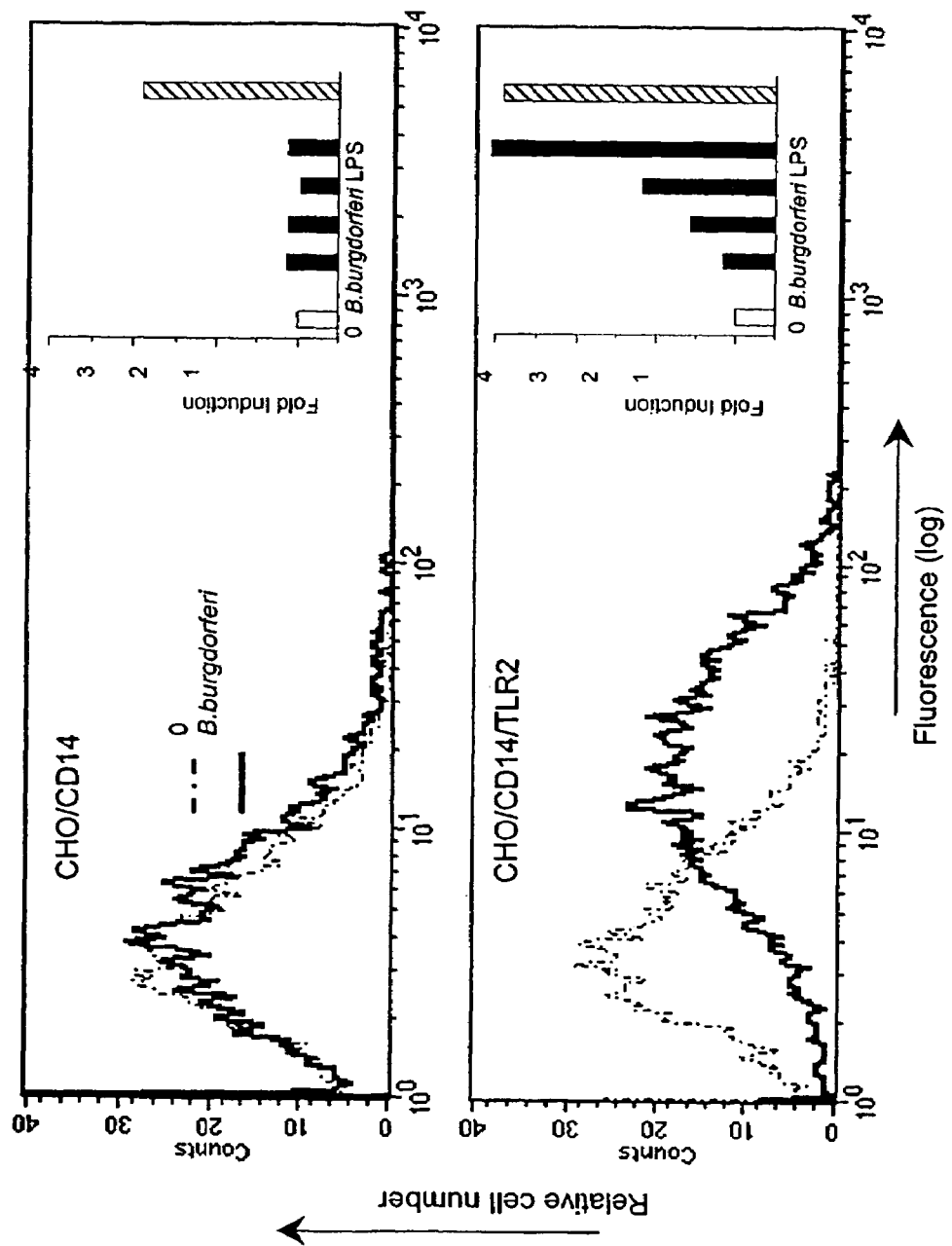
Figure 9B:
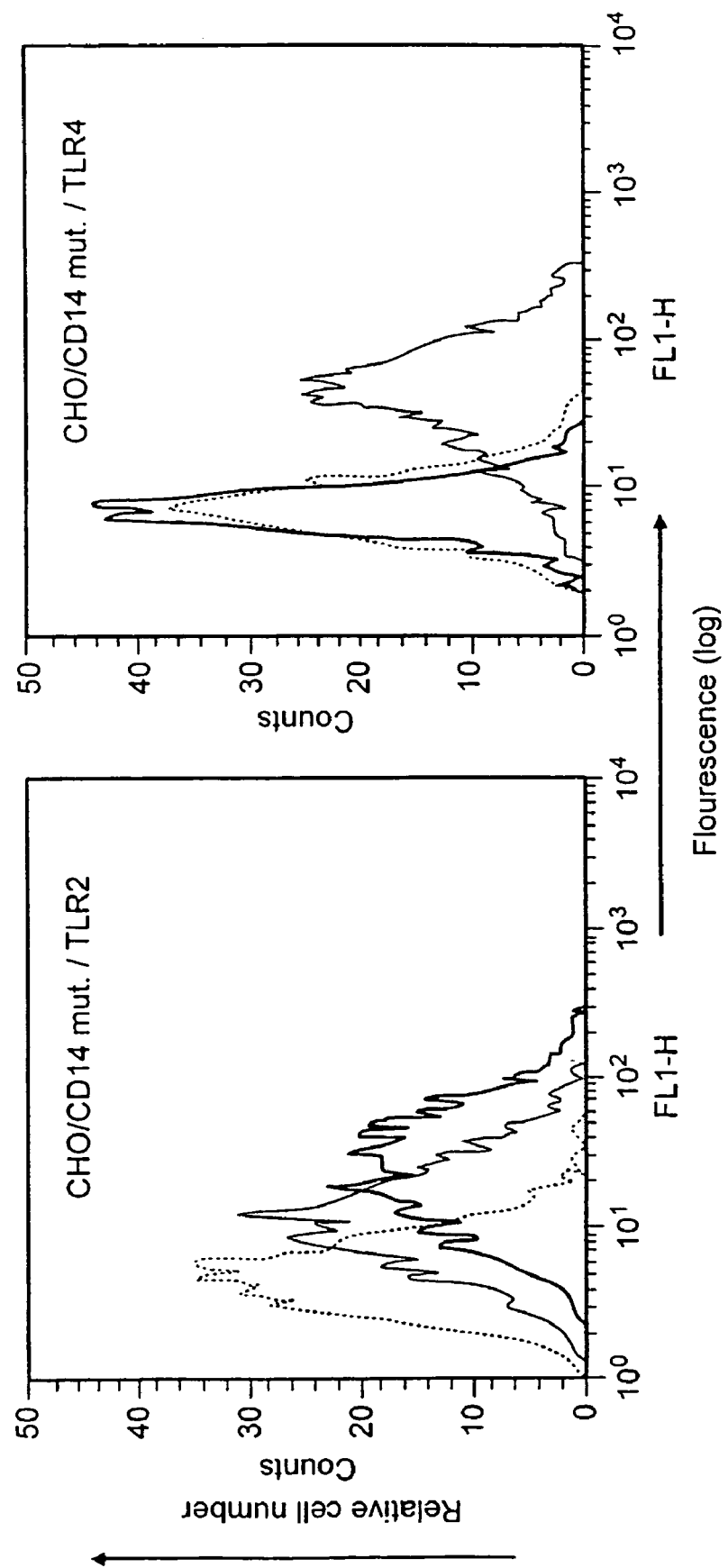

FIG. 9 is a set of graphs showing that TLR2 mediates cellular activation upon exposure to live B. burgdorferi. FIG. 9A. CHO/CD14 or CHO/CD14/TLR2 cells were left untreated (dotted lines) or exposed to motile B. burgdorferi (thick lines, 1000 spirochetes/cell=2.5×107 spirochetes/ml) for 8 hours. The cells were harvested, stained for reporter gene expression and analyzed by flow cytometry, as described in FIG. 7. Indicated in inserts is the fold increase of median fluorescence relative to unstimulated cells (fold induction plotted against bacteria, LPS). From left to right: untreated cells (0, open bars), cells exposed to different doses of live B. burgdorferi (dark bars: 1, 10, 100 and 1000 spirochetes/cell, respectively) and LPS (hatched bars, 100 ng/ml) FIG. 9B. LPS non-responder mutant CHO/CD14 cells transfected with TLR2 or TLR4 were exposed to medium (dotted lines), 1000 spirochetes/ml (thick lines) or LPS (thin lines, 100 ng/ml). One representative out of three experiments performed is shown. In FIGS. 9A and 9B relative cell number (counts) is plotted against fluorescence (log).

Figure 10A:
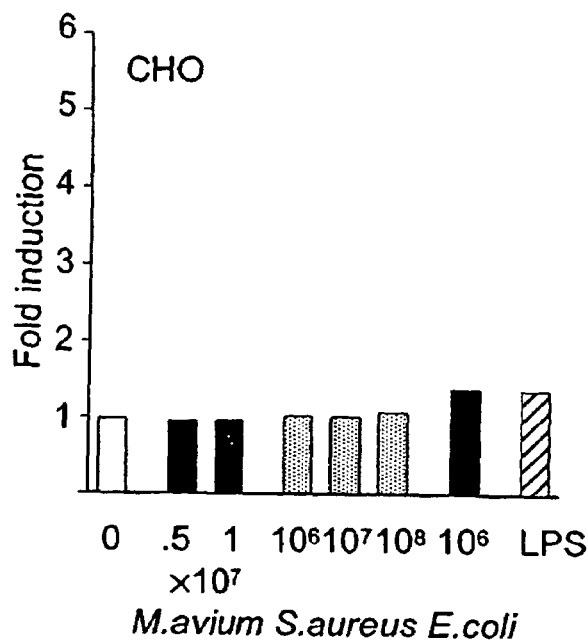
Figure 10B:
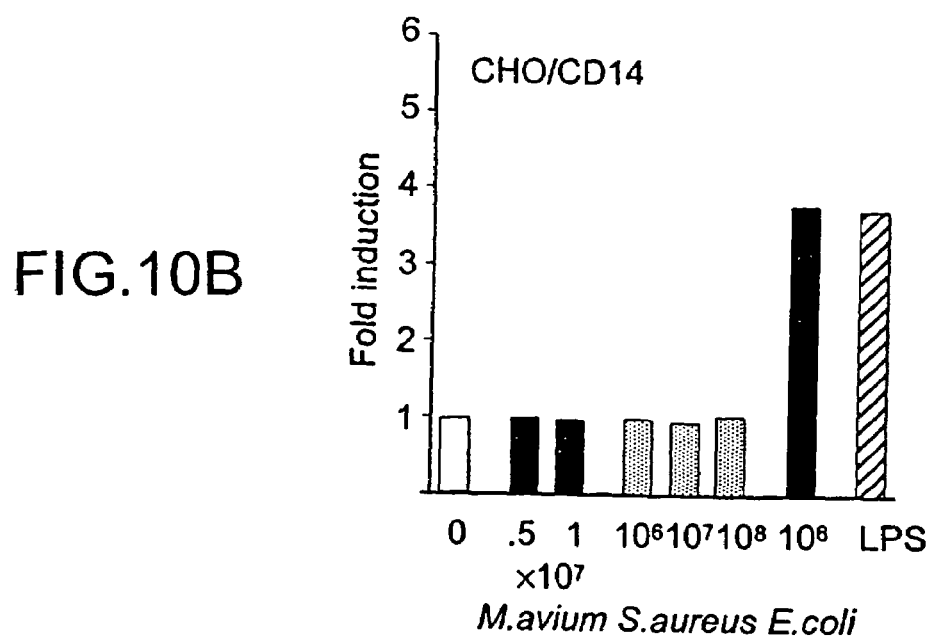
Figure 10C:
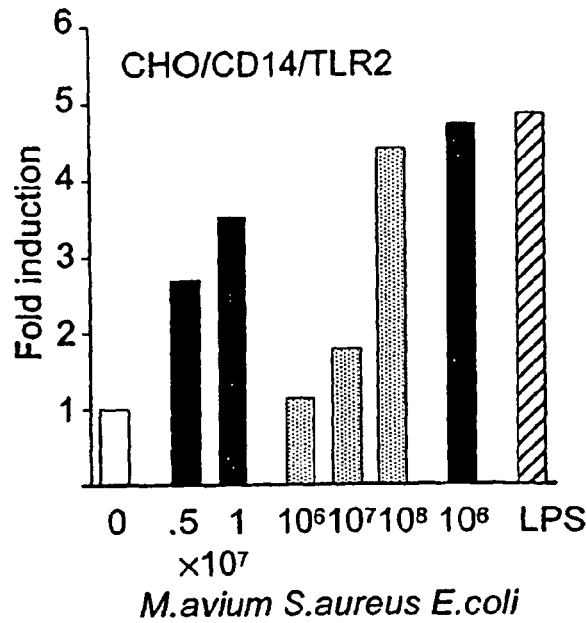

FIG. 10 is a set of graphs showing microbial pattern recognition via CD14 and TLR2. CHO control (A), CHO/CD14 (B) or CHO/CD14/TLR2 (C) reporter cell lines were exposed to the following stimuli (from left to right): medium (0, open bars), live M. avium (dark bars), heat-killed S. aureus (gray bars), E. coli bio-particles (light gray bars) or LPS (hatched bars, 100 ng/ml). Numbers on the x axis indicate the density of the bacteria per ml. After 20 hours, the cells were harvested, stained for reporter gene expression and analyzed by flow cytometry, as described in FIG. 7. The y-axis indicates fold increase of median fluorescence (fold induction) compared to unstimulated cells. Shown is one representative experiment out of three performed.

Figure 11B:
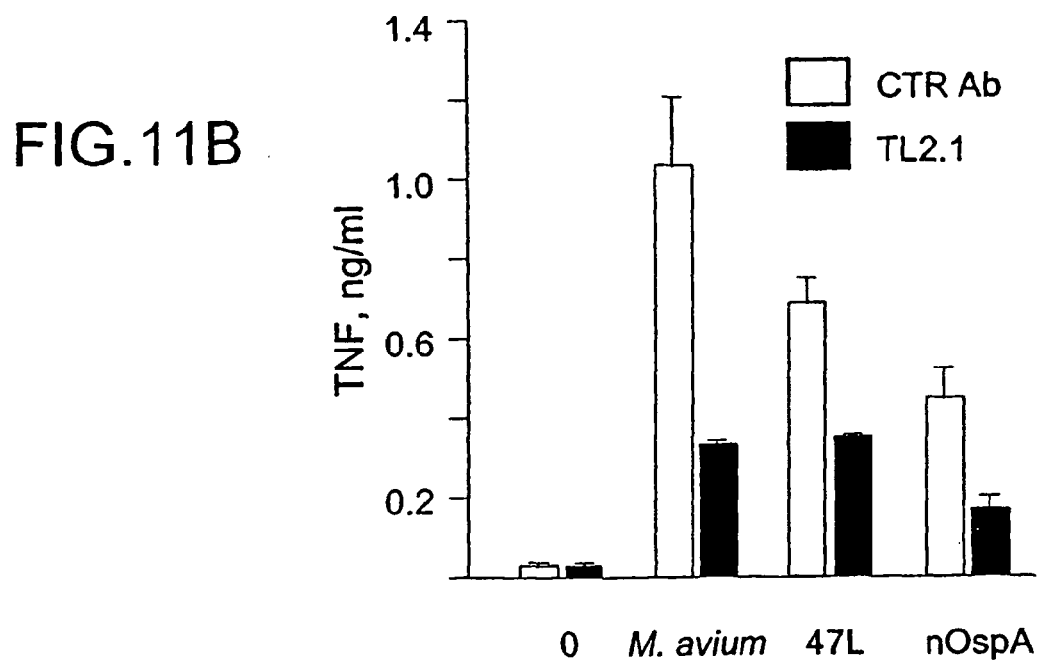
Figure 11A:
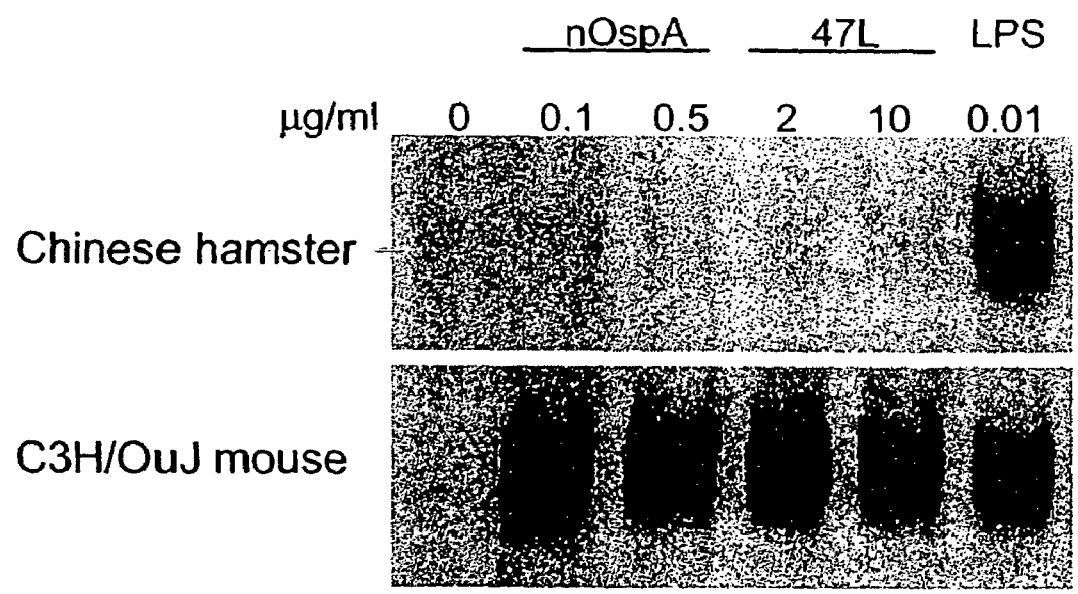

FIG. 11A shows a gel and FIG. 11B shows a graph and from this it can be deduced that TLR2 mediates responses to lipoproteins/lipoptides in primary cells. In FIG. 11A, TLR2-null peritoneal macrophages from Chinese hamsters and C3H/OuJ mice were stimulated with nOspA, 47L and LPS for 1 hr in RPMI 1640 medium containing 10% FBS. Nuclear extracts were isolated and analyzed for binding to a NF-κB specific probe by electrophoretic mobility shift assay. Shown is the NF-κB band, in one representative experiment out of two performed. In FIG. 11B, Human PBMC were isolated by gradient centrifugation, resuspended in RPMI 1640 medium containing 10% human serum and plated at a density of 7×105/well in a 96 well dish. The mouse anti-human TLR2 antibody TL2.1 or control antibodies (mouse IgG) were added to a final concentration of 5 µg/ml, and the cells were exposed to *M. avium* ($5 \times 10^6$ bacteria/ml), 47L (1 µg/ml) or nospA (300 ng/ml) in a total volume of 0.2 ml for 12 hours. The supernatants were harvested and assayed for TNF by immunoassay. The antibody did not block activation induced by phorbol ester (not shown). Data are from one experiment representative of three performed. Given is mean of duplicate wells +/−SD. Concentration of TNF (ng/ml) is shown on the y axis against bacteria on the x axis.

Figure 12:
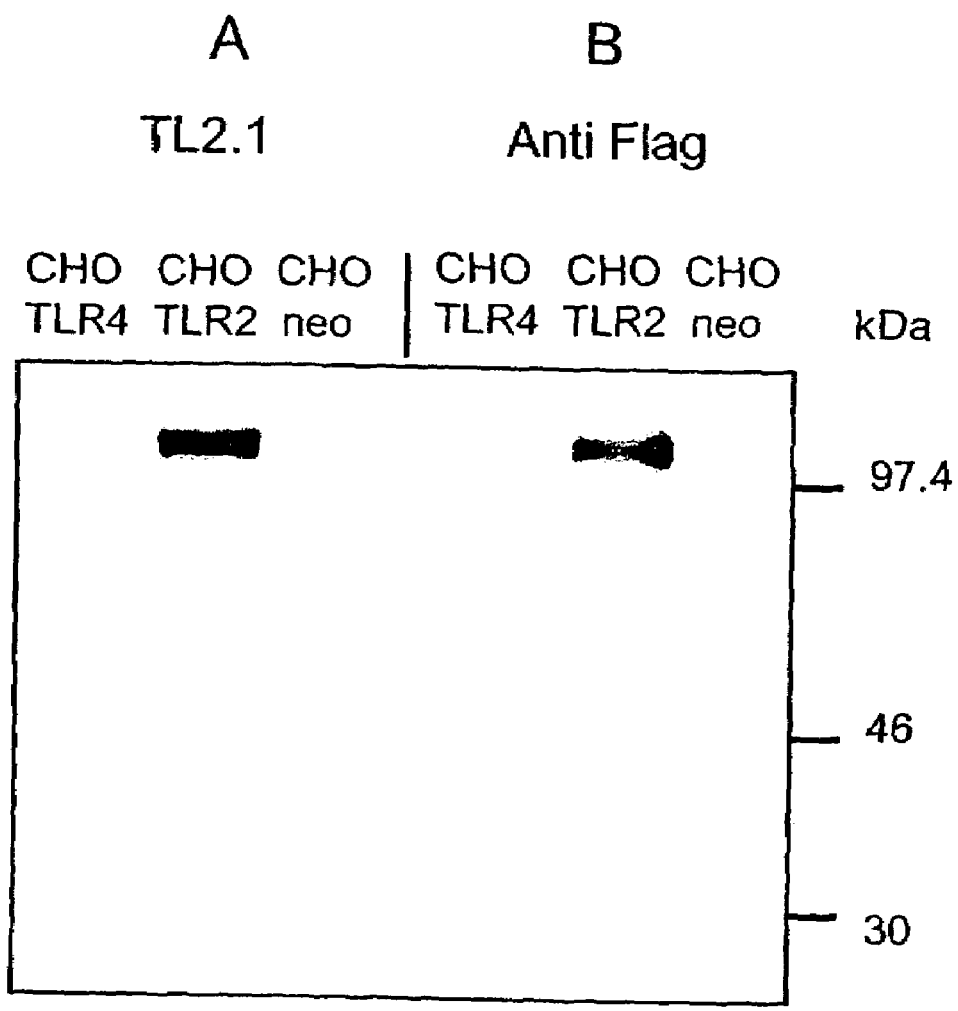

FIG. 12 shows Western blots of lysates from different CHO cells. In A the lysates were immuneprecipitated with the TL2.1 mab, and in B the lysates were precipitated with a FLAG antibody which detects a FLAG epitope that has been inserted in the TLR2 protein by making a FLAG-TLR2 plasmid construct. As demonstrated in the figure, the TL2.1 and the Flag antibody detect a protein with similar molecular weight, which strongly support that TL2.1 indeed has a specificity for the TLR2 protein.

Figure 13:
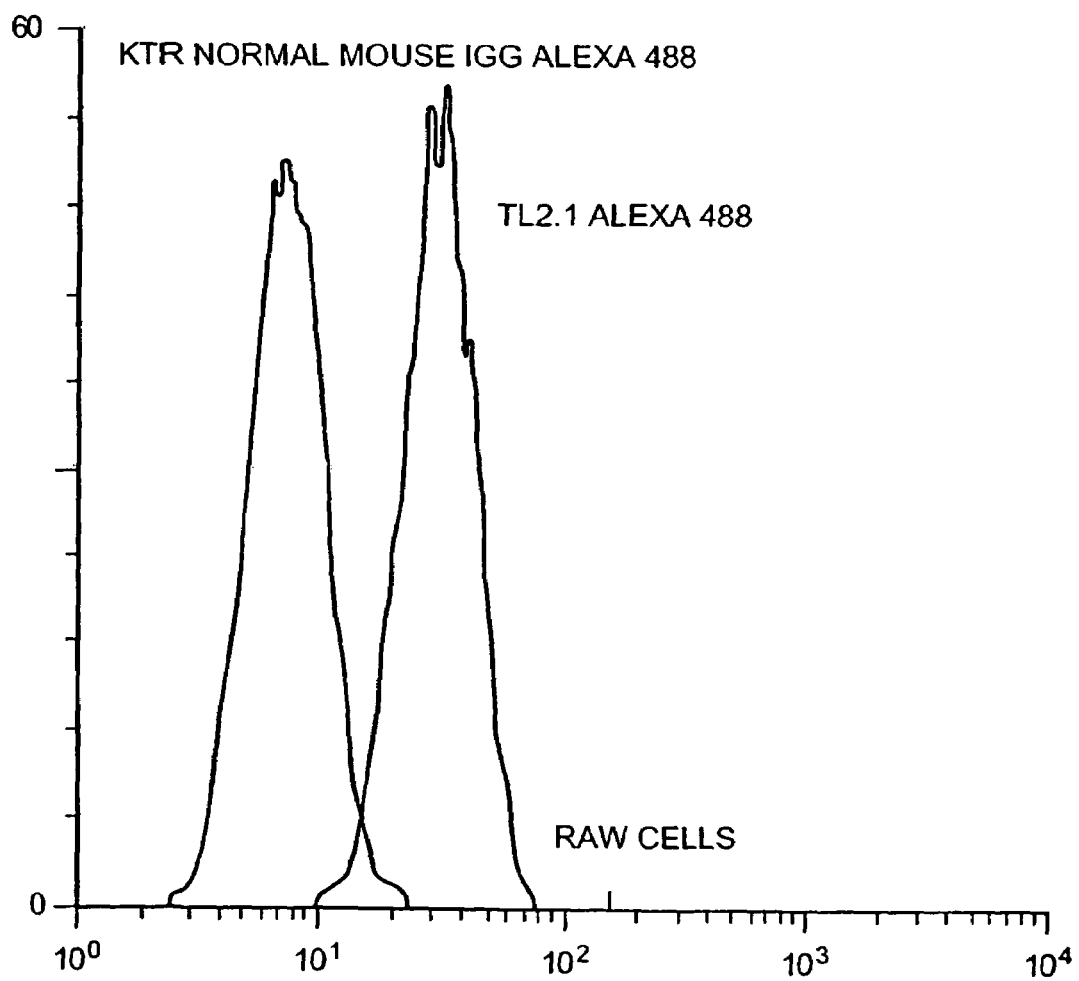

FIG. 13 is a flow cytometric histogram of binding of TL2.1 to murine RAW 264.7 macrophage cells. TL2.1 was labelled with Alexa 488 and added to the cells for 30 minutes prior to analysis. The x-axis represents increasing fluorescence (log. scale), the y-axis represents number of cells. 5000 cells were analysed in this histogram.

FIG. 14 is a graph showing the inhibitory effect of TL2.1 mabs on TNF production induced by *M. Tuberculosis* in macrophages isolated from the peritoneal cavity of C3H/HeJ mice. On the y axis, TNF concentration (µg/ml) is plotted against strain of *M. Tuberculosis* (M=b Ra and M+b Rv) on the x axis, in the presence of murine macrophages: dark grey HeJ; light grey=HeJ+anti-TLR2 antibody; white=HeJ+ctrl 1 g (control antibody).

FIG. 15 shows inhibition by TL2.1 of TNF production from human monocytes stimulated with mannuronic acid polymers (poly M). The monocytes were isolated from human blood. 10 µg/ml of mabs were added together with the stimulus and after 6 hours supernatants were harvested and assayed for TNF content. The histogram shows TNF (pg/ml) for each sample of monocytes, either control or to which antibodies had been added (medium control; TLR2 Mabs; CD15 Mabs; control Mab).

Figure 16A:
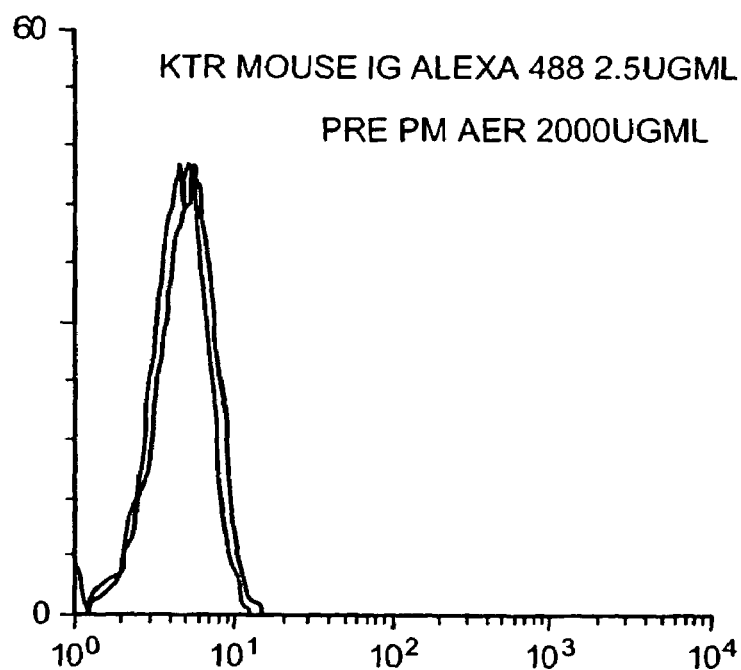
Figure 16B:
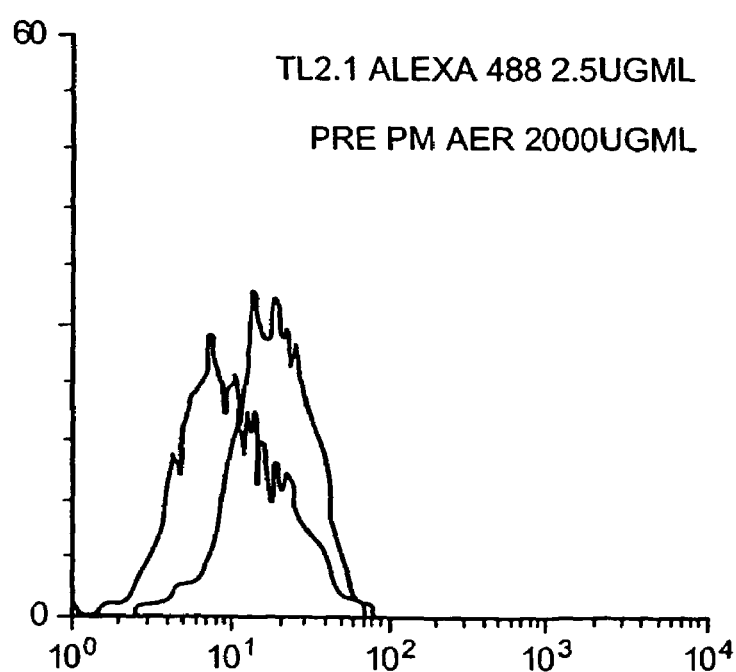

FIG. 16 presents flow cytometry histograms showing the effects of mannuronic acid polymer (polyM) in inhibiting the binding of antibody TL2.1 to human PBMC (FIG. 16B) as compared with a control antibody (FIG. 16A). The cells (PBMC) were preincubated with the polymer (2000 µg/ml) for 1 hour on ice before 25 µg/ml Alexa 488 labelled TL2.1 was added and incubated for an additional 1 hour on ice. The samples were then run on a FacsScan flow cytometer, with 5000 cells in each histogram (B). In A, the controls with an irrelevant mouse antibody are shown. The x-axis represents increasing fluorescence (log. scale), the y-axis represents number of cells.

Figure 17:
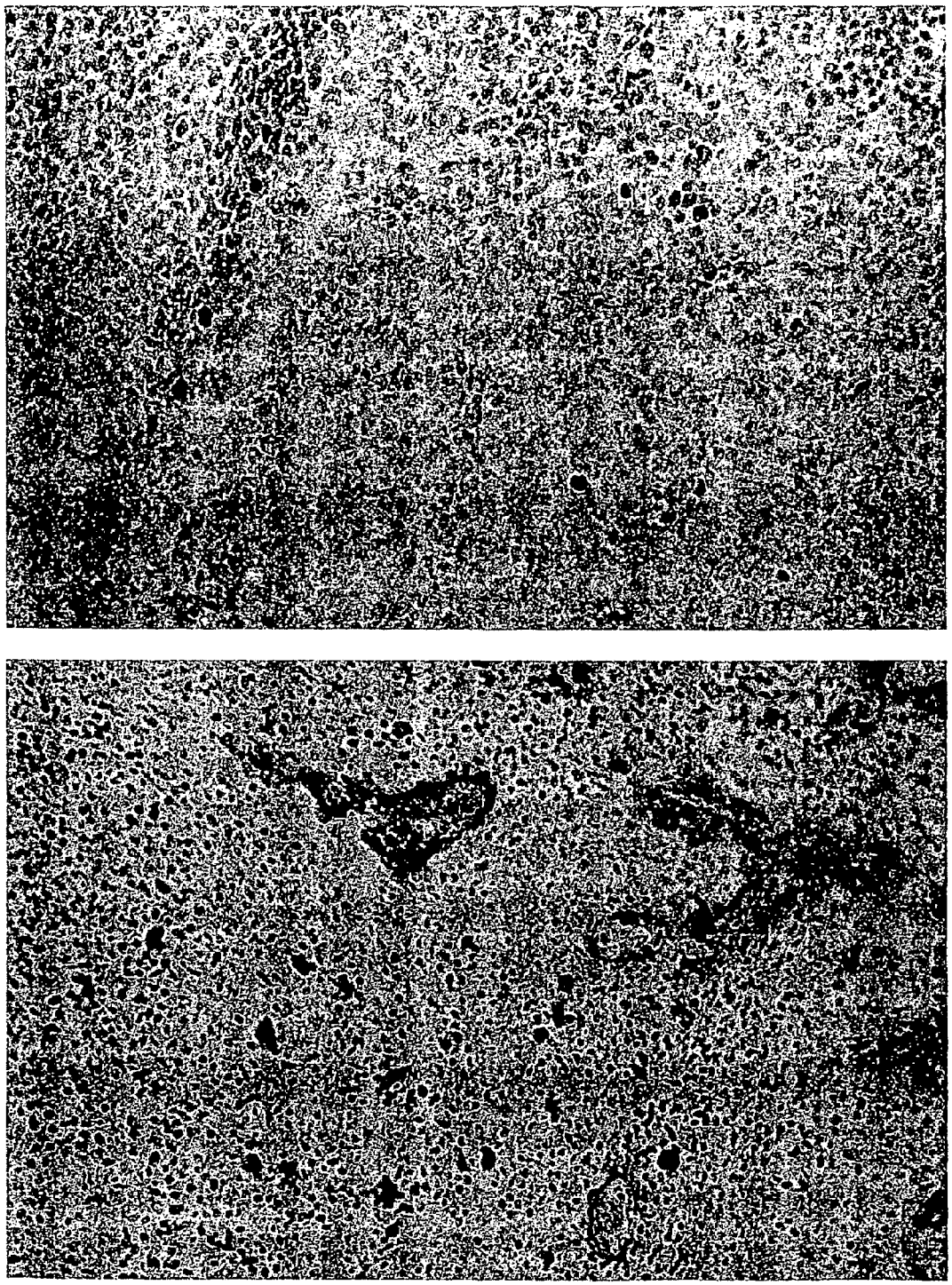

FIG. 17 is a freeze section of human tonsil tissue showing scattered cells positive for TLR2. The sections were stained by standard immunohistochemical procedures using the TL2.1 as a primary antibody. The positive cells are likely to represent tissue macrophages.

EXAMPLE 1

Human Toll-Like Receptor 2 Mediates Monocyte Activation by *Listeria Monocytogenes*, but not by Group B Streptococci The purpose of this experiment is to investigate whether TLR2 can signal cell activation by the heat killed group B *streptococcus* type III (GBS) and *Listeria monocytogenes* (HLKM). The Example also describes the generation of Mab antibody TL2.1 and its functional effects on TLR2-activated signalling by LPS and HKLM.

Reagents

LPS (L-2137) from smooth *Salmonella* minnesota was purchased from Sigma (St. Louis, Mo.). COH-1, an encapsulated type III GBS strain, was kindly provided by Craig Rubens, University of Washington, Seattle. *Listeria monocytogenes* was from a recent clinical isolate. Bacteria were grown to the early stationary phase in Todd-Hewitt broth, killed by heat-treatment (60° C. for 45 min), washed extensively with distilled water and lyophilized. Human CD14 mAb 3C10 (IgG2b. ATCC, Manassas, Va.) and the mAb 6H8 (IgG1), that recognizes a widely distributed 180 kDa glycoprotein (T. Espevik and B. Naume, unpublished observation), were purified from supernatants of the respective hybridoma cell lines on Sepharose goat anti-mouse IgG as described by the manufacturer (ZYMED Lab. Inc., San Fransisco, Calif.). Recombinant human TNF (specific activity of $7.6*10^7$ U/mg) was supplied by Genentech Inc. (South San Francisco, Calif.), and recombinant human IL-6 (specific activity of $>1*10^8$ U/mg) was purchased from Genzyme Pharmaceuticals (Cambridge, Mass.).

Cell Lines and Culture Conditions

The following stable transfected CHO-K1 fibroblast cell lines were generated, or have been described elsewhere. CHO-CD14: CHO-K1 transfected with human CD14 (Golenbock et al., (1993). *J. Biol. Chem.* 268:22055–22059). CHO-neo: CHO-K1 transfected with pcDNA3/neo (Invitrogen, San Diego, Calif.); CHO-TLR2 and CHO-TLR4: TLR2 and TLR4 cDNAs cloned into a pFLAG vector (Kirschning et al., (1998) *J. Exp. Med.* 188:2091–2097), gifts from C. Kirschning and M. Rothe (Tularik. Inc., San Fransisco, Calif.), were transfected into CHO-K1 cells together with pcDNA3/neo (Yoshimura et al., *Ju. Immuno.* 163:1–5) or pEGFP1/neo (Clontech, Palo Alto, Calif.), respectively. Stable transfectants were selected by cell sorting and limiting dilution cloning. All transfectants were maintained in RPMI 1640 medium (Gibco, Paisley, UK) with 0.01% L-glutamine, 40 µg/ml gentamycin (referred to as RPMI), 10% heat inactivated FCS (HyClone, Logan, Utah) and 0.5 mg/ml G418 (Sigma) at 37° C. and 5% $CO_2$.

Generation of Nuclear Extracts and Electrophoretic Mobility Shift Assay (EMSA)

Transfected CHO cells were seeded in 6-well plates at a density of $3 \times 10^5$ cells/well and incubated over night. Monolayers were then washed twice in Hanks Balanced Salt Solution (HBSS) (Gibco) and treated with different stimuli in 1 ml RPMI/2% human serum (HS) A+ (University Hospital, Trondheim, Norway) for the indicated period of time. Nuclear extracts were prepared and analyzed for NFκB binding activity with a $^{33}$P end-labelled NFκB-specific oligonucleotide probe as previously described (Medvedev et al., (1998), *J. Immunol.* 160:4535–4542), except that autoradiography was performed with a PhosphoImager SF system (Molecular Dynamics, Sunnyvale, Calif.). The intensity of the bands was quantitated by use of ImageQuant® software, and results are presented as relative units.

IL-6 Assay

CHO-cells were plated at a density of $2.5 \times 10^4$ cells/well in 24-well dishes. After an overnight incubation the cells were washed two times with HBSS, and exposed to different stimuli in RPMI 5% HS for 14 h at 37° C. In some experiments, cells were pretreated with 10 µg/ml of a TLR2 mAb (TL2.1) or a control mAb (6H8) for 30 min at RT prior to addition of the stimuli. Supernatants were collected and stored at −20° C. until assayed for IL-6 content by the B9 cell proliferation assay (Aarden et al., (1987), *Eur. J. Immunol.* 17:1411–1416). Results from representative experiments are presented as mean±SD of triplicate IL-6 measurements.

Generation of the TLR2 mAb. TL2.1

Three Balb/c mice (Blomholt Gaard, Denmark) were injected intraperitoneally with $10^6$ CHO-TLR2 cells suspended in 0.5 ml PBS on day 0, 14 and 27. Blood samples were obtained from the thighs on day 0 and 40, and the binding of serum antibodies to human PBMC and CHO-TLR2 cells was analyzed by flow cytometry. One mouse was selected and boosted with $10^6$ CHO-TLR2 cells intraperitoneally four and three days before sacrifice. Hybridomas were generated by fusion of mouse spleen cells and NSO myeloma cells (generously provided by Dr. Z. Eshhar, The Weizmann Institute of Science, Israel), and seeded in 96-well plates with HAT-selection (Kohler, et al., (1975), *Nature* 256:495–497). Hybridoma supernatants were screened for antibody-production and specific TLR2 binding by flow cytometry. The strategy of the selection procedure was:

1. Screen all hybridomas (approximately 700) for immunoglobulin production.
2. Positive hybridomas (approximately 160) were then tested for binding to PBMC.
3. Positive hybridomas secreting antibodies that bound to PBMC (approximately 60) were tested for binding to CHO-TLR2 cells.
4. Positive hybridomas for CHO-TLR2 cells (4) were tested on control cells (CHO-neo transfected and CHO transfected with TLR4).
5. One hybridoma produced an antibody named TL2.1 (IgG2a) which was found to be specific for CHO-TLR2 only i.e. it did not bind to CHO-neo and CHO-TLR4 cells.

The hybridoma producing an antibody named TL2.1 (IgG2a) was then subjected to two rounds of limiting dilution cloning to secure monoclonality. TL2.1 was purified on Sepharose goat anti-mouse IgG as described by the manufacturer (ZYMED).

Flow Cytometry Analysis

All steps were performed at 0–4° C. Adherent CHO transfectants were detached by trypsin/0.02% EDTA/PBS, washed twice in PBS/1% heat inactivated FCS (PBS/FCS) and incubated with anti-FLAG M2 mAb (Sigma) or PBS/FCS for 45 min. After two washes, the cells were labeled for 30 min with either FITC-conjugated goat anti-mouse mAbs (FITCGAM, Becton Dickinson, Lincoln Park, N.J.), a CD14 mAb (FITC-LeuM3, Becton Dickinson), or the TLR2 mAb (TL2.1) conjugated to Alexa 488 fluorochrome (Molecular Probes, Eugene, Oreg.). PBMC were isolated from human A+ buffy coats (The Bloodbank, University Hospital, Trondheim, Norway) by Lymphoprep (Nycomed, Oslo, Norway) density gradient centrifugation, washed four times in HBSS and once in PBS/FCS, and labeled with Alexa 488-conjugated TL2.1, PE-conjugated CD14 mAb 18D11 (Diatec AS, Oslo, Norway), or both for 30 min. Cells were then washed twice and analyzed with a FACscan flow cytometer (Becton Dickinson).

Metabolic Labeling

CHO cells were seeded in 6-well plates and grown to 50–90% confluence. The adherent cells were washed twice with PBS, and labeled with 80–100 µCi TRAN$^{35}$S-LABEL/well (ICN, Costa Mesa, Calif.) in methionine- and cysteine-free DMEM (ICN) containing 10% dialyzed FCS for 16 h at 37° C., 8% $CO_2$. All the subsequent steps were performed at 0–4° C. Cells were washed once in ice-cold PBS and lysed for 10 min with 400 µl lysis buffer/well (50 mM Tris, 150 mM NaCl, 0.1% BSA, 1% Igepal CA630 (Sigma), 0.5 mM PMSF, pH 7.5). Cell lysates were transferred to Eppendorf tubes and spun down at 10 000 g for 10 min to remove cell debris. The lysates were precleared by incubation with 100 µl Sepharose goat anti-mouse IgG for 30 min. and the supernatants were split into two and immunoprecipitated over night with 50 µl of either TLR2 mAb (TL2.1) or control CD14 mAb (3C10) attached to Sepharose goat anti-mouse IgG (5 µg mAb/1 ml Sepharose). Precipitated samples were washed three times in (50 mM Tris, 0.5 M NaCl, 0.1% BSA, 0.2% Igepal CA630, pH 7.5), twice in (50 mM Tris, 0.2% Igepal CA630, pH 7.5) and separated by SDS gel electrophoresis on a 8% gel. Gels were fixed, incubated in Amplify solution (Amersham Life Science, Buckinghamshire, UK) for 30 min and dried before exposure to Kodak MR film at −70° C.

Stimulation of Monocytes

Adherent cell monolayers ($1-2 \times 10^5$ monocytes/well in 24 well dishes) were prepared from PBMC as previous described (Espevik T., (1985), *J. Immunol.* 134:2017–2025). The cells were washed three times in HBSS before addition of 10 µg/ml of TLR2 mAb (TL2.1), CD14 mAb (3C10), combination of TL2.1 and 3C10, or a control mAb (6H8) for 30 min at RT in RPMI. After addition of the indicated stimuli, incubation proceeded for 8 hours at 37° C. before supernatants were collected and stored at −20° C. until assayed for TNF-activity in the WEHI 164 clone 13 bioassay, as described (Espevik et al., (1986), *J. Immunol. Methods* 95:99–105). Results' from one representative experiment are presented as mean±SD of triplicate TNF measurements.

Results

HKLM Induce IL-6 Production from CHO-TLR2 Cells, But not CHO-CD14 Cells

Recently, CHO-K1 cells were shown to express mRNA encoding a truncated and non-functional TLR2 (Heine et al., (1999), *J. Immunol.* 162:6972–6975). Based upon this, and recent studies that suggest TLR2 involvement in cellular responses to Gram-positive bacteria (Yoshimura et al., (1999), *J. Immunol.* 163:1–5; Schwandner et al., (1999) *J. Biol. Chem.* 274:17406–17409), we examined the ability of HKLM and GBS to activate CHO cells transfected with human TLR2. CHO-neo, CHO-CD14 and CHO-TLR2 cells were exposed to HKLM, GBS or LPS for 14 h in the presence of 5% HS, and IL-6 production was measured in supernatants.

As shown in FIG. 1, LPS induced IL-6 production from CHO-CD14 and CHO-TLR2 cells with similar potency. Addition of HKLM resulted in IL-6 production from CHO-TLR2 cells, but not CHO-CD14 cells (FIG. 1). GBS did not induce IL-6 production in neither CHO-TLR2 cells nor in CHO-CD14 cells (FIG. 1). The results indicate that TLR2-expression is sufficient and necessary for activation of CHO cells by HKLM, whereas neither TLR2 nor CD14 make CHO cells responsive to GBS. LPS activates cells in a CD14-dependent manner (Wright-et al., (1990), *Science* 249:1431–1433; Golenbock et al., (1993), *J. Biol. Chem.* 268:22055–22059; Fenton et al., (1998), *J. Leukoc. Biol.* 64:25–32), and CHO-CD14 cells respond to LPS in the absence of TLR2 (Heine et al., supra). Thus, CD14 or TLR2 are sufficient, but not necessary, for LPS-induced activation of CHO cells.

HKLM Induce a Time- and Dose-dependent Translocation of NFκB in CHO-TLR2 Cells

In the next series of experiments, CHO-neo and CHO-TLR2 cells were incubated together with increasing amounts of GBS, HKLM or LPS for the indicated period of time in the presence of 2% human serum (HS) before nuclear extracts were isolated and analyzed for translocation of the transcription factor NFκB.

Figure 2A:
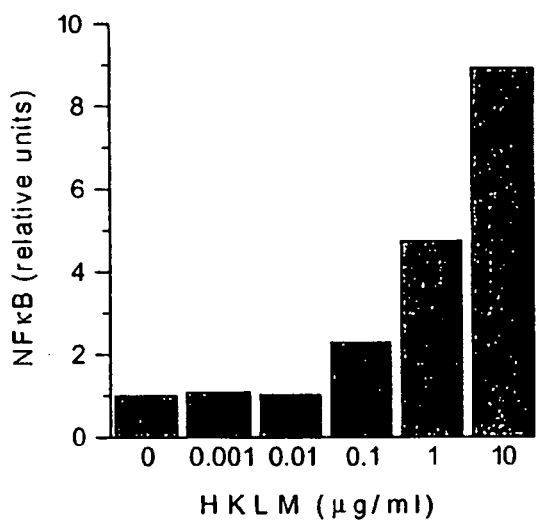
Figure 2A:
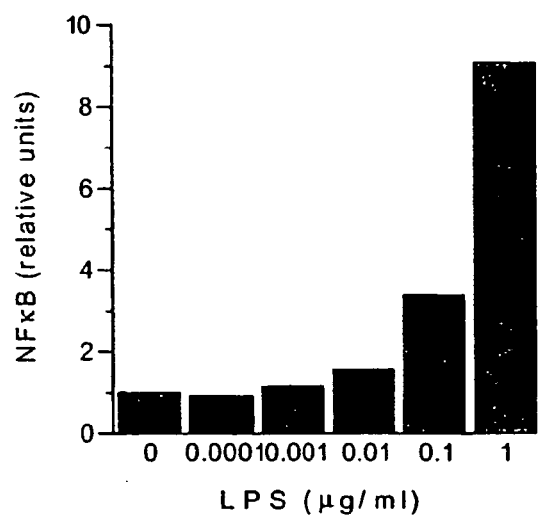
Figure 2A:
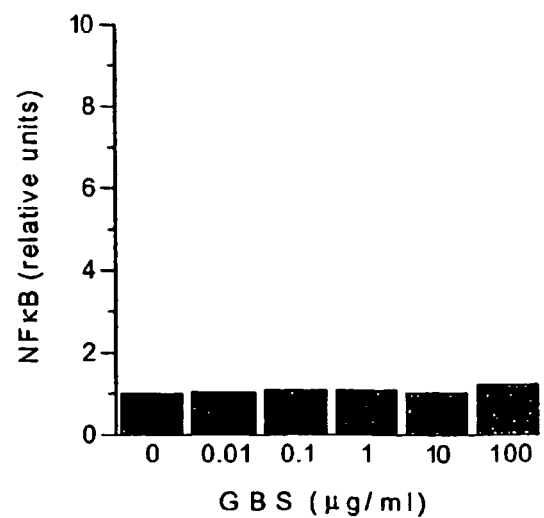

As shown in FIG. 2A, both HKLM and LPS induced a dose-dependent NFκB-activation of CHO-TLR2 cells (FIG. 2A). GBS failed to induce NFκB activation in CHO-TLR2 cells, even at a concentration of 100 μg GBS/ml (FIG. 2A). Control CHO-neo cells were unresponsive to HKLM and GBS, and were hyporesponsive to LPS, comparable to the data presented in FIG. 1 (data not shown).

Figure 2B:
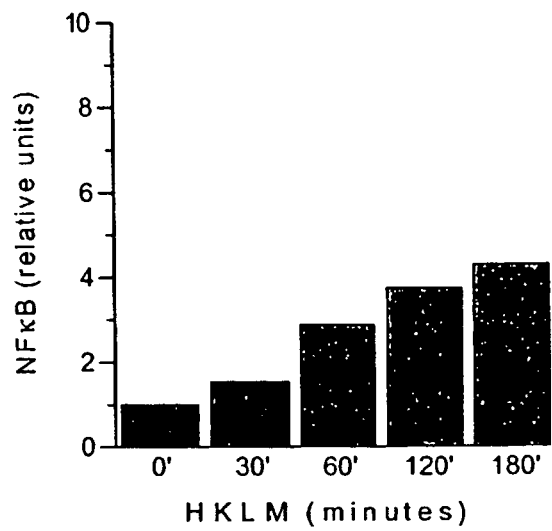
Figure 2B:
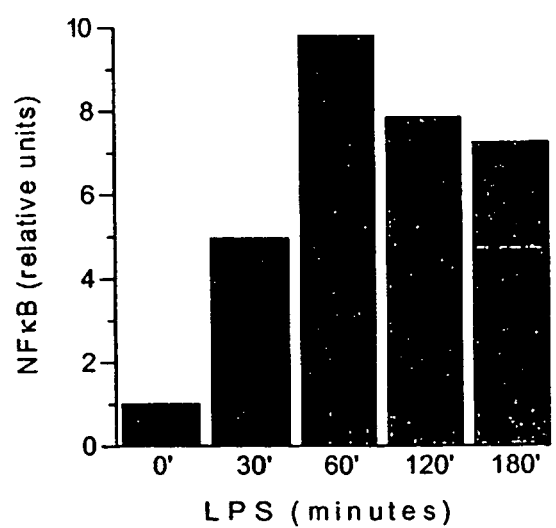
Figure 2B:
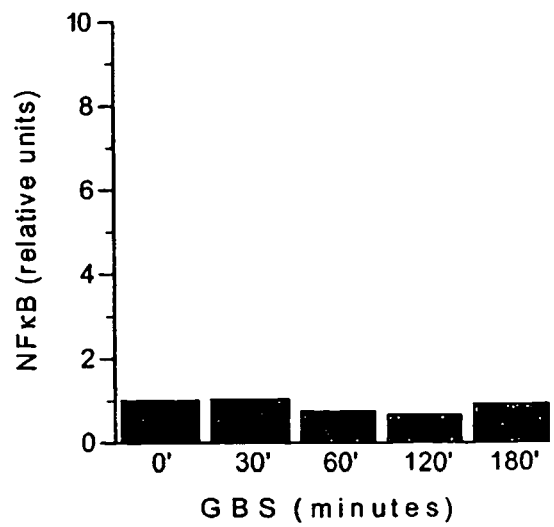

The time-course of HKLM- and LPS-induced NFκB activation of CHO-TLR2 cells differed. Detectable NFκB translocation was seen after 30 min. of stimulation with LPS, which reached a maximum after 60 min. and thereafter declined (FIG. 2B). HKLM also induced NFκB activation by 30 min., but in contrast to LPS the response continued to increase during the 180 min. period of stimulation (FIG. 2B). In accordance with the results in FIG. 1A, GBS did not activate CHO-TLR2 cells at any time points measured (FIG. 2B). These data suggest that TLR2 differs in the way of recognizing these two types of Gram-positive bacteria.

Generation of the TLR2 mAb, TL2.1

To study the biological significance of TLR2 in responses to HKLM, LPS and GBS, hybridomas producing mAbs recognizing TLR2 were generated. The mAb TL2.1 showed profound binding to CHO-TLR2 cells, but not to CHO-neo, CHO-CD14 or CHO-TLR4 cells (FIG. 3A) suggesting that this mAb specifically recognized TLR2. Controls with mAbs to the FLAG-tag or to CD14 confirmed that the cells expressed FLAG-TLR2, FLAG-TLR4 or CD14, respectively, and the lack of binding of TL2.1 to CHO-TLR4 cells further indicate that TL2.1 is not directed towards the FLAG epitope.

To further establish the specificity of TL2.1 for TLR2, lysates from $^{35}$S-labelled CHO-neo, CHO-TLR2 and CHO-TLR4 cells were immunoprecipitated with TL2.1 or a CD14 control mAb, 3C10, and subjected to SDS gel electrophoresis. As shown in FIG. 4, a protein band of ~98 kDa appeared only in the CHO-TLR2 lysate immunoprecipitated with TL2.1. Calculated from the amino acid sequence (Rock et al., (1998), *Proc. Natl. Acad. Sci.* 95:588–593), the molecular weight of FLAG-TLR2 is about 85 kDa, and the observed mobility in gels corresponding to ~98 kDa may be due to glycosylation of the protein.

Figure 3A:
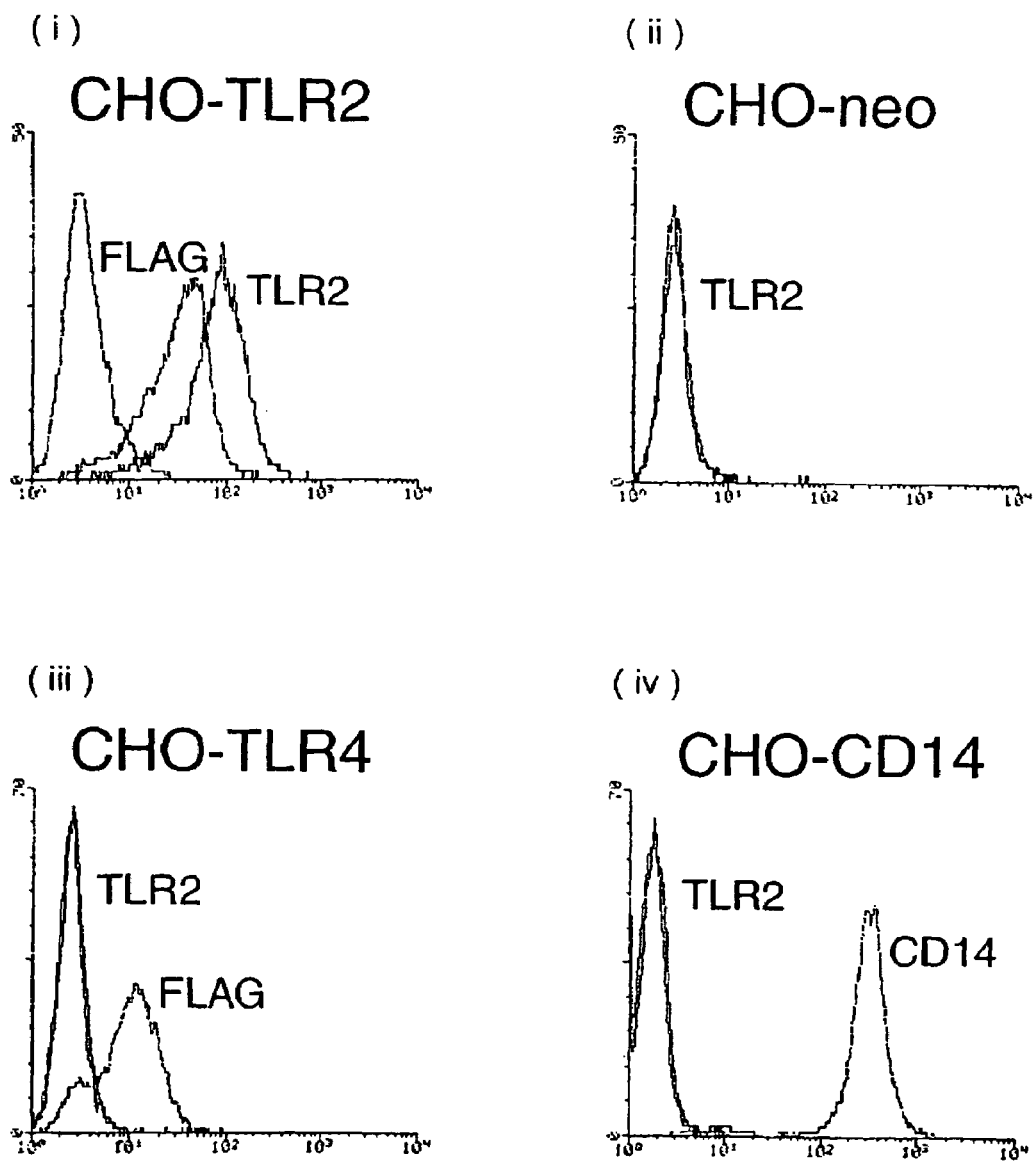
Figure 3B:
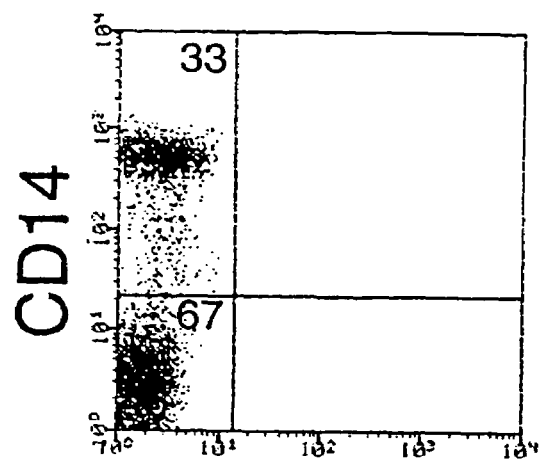
Figure 3B:
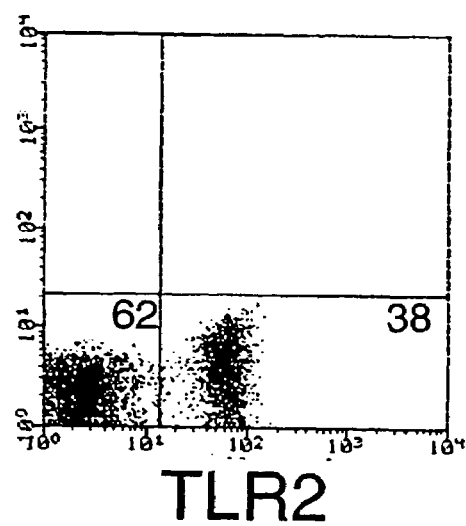
Figure 3B:
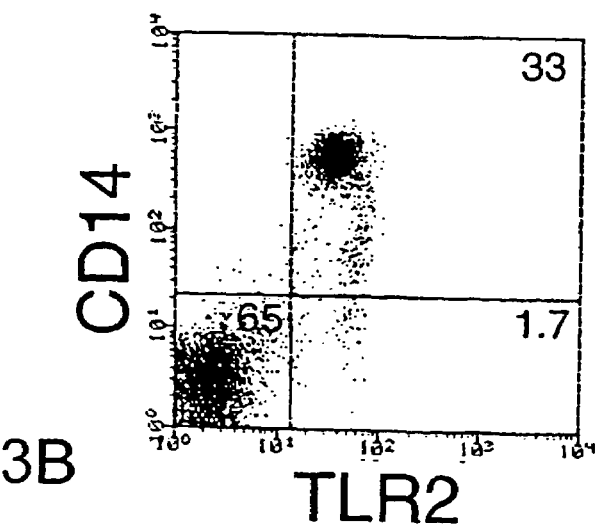

We further compared the expression of TLR2 and CD14 on peripheral blood mononuclear cells (PBMC) by incubating PBMC with Alexa 488-labeled TL2.1 and a PE-labeled CD14 mAb (18D11). As shown in FIG. 3B, TLR2 co-localized with CD14 and less than 2% of the PBMC were TLR2+/CD14−. Thus, in PBMC the expression of TLR2 is almost entirely restricted to monocytes, reinforcing the assumptions that TLR2 serves a role in human innate immunity.

TL2.1 Inhibits HKLM- and LPS-Induced IL-6 Production from CHO-TLR Cells

In order to examine the ability of TL2.1 to specifically block TLR2-mediated cell activation, CHO-TLR2 and CHO-CD14 cells were pre-treated with TL2.1 or a control mAb (6H8) prior to addition of HKLM or LPS. Results in FIG. 5 show that TL2.1 inhibited both HKLM- and LPS-induced IL-6 production from CHO-TLR2 cells with about 60%, but had no inhibiting effect on the LPS-induced activation of CHO-CD14 cells. The control mAb, 6H8, did not affect the IL-6 production induced in either cell transfectants. These data show that the TL2.1 mAb interacts with a TLR2 epitope that is involved in HKLM- and LPS signaling in CHO-TLR2 cells.

HKLM Activate Human Monocytes Through a TLR2- and CD14-Dependent Pathway

In the next experiments we studied the inhibitory action of the TLR2 mAb (TL2.1) and a CD14 mAb (3C10) on TNF-production from human monocytes stimulated with HKLM, GBS or LPS at serum-free conditions. Both TL2.1, and to a lesser extent 3C10, independently inhibited HKLM-induced TNF-production, but combining the two mAbs were more effective in blocking the response than adding them individually (FIG. 6). The data indicate that both CD14 and TLR2 are involved in mediating HKLM-induced TNF-production from monocytes. Neither TL2.1 nor 3C10 inhibited the GBS-induced TNF-production from monocytes (data not shown), which confirm the earlier observations that different mechanisms mediate cell activation by HKLM and GBS.

As previously reported (Wright et al., (1990), *Science* 249:1431–1433), the CD14 mAb 3C10 completely blocked LPS-induced TNF-production from monocytes, but the TLR2 mAb TL2.1 did not inhibit TNF production induced by the smooth LPS from *Salmonella minnesota* used in this study (FIG. 6).

Thus, although TLR2 could mediate LPS-activation of CHO-cells, this is not the main signalling pathway for LPS-induced activation of the more biologically significant manocytes expressing the main subset of suggested LPS receptors.

Conclusions

The present study shows that TLR2 can mediate cell activation by one Gram-positive pathogen, *Listeria monocytogenes*, but not by another, Group B *Streptococcus*. Thus, human TLR2 discriminates between similar classes of pathogens.

By making a blocking mAb to TLR2, we found that although TLR2 mediates LPS-activation in transfected cell lines, this does not seem to be the main pathway of generating a TNF response in human monocytes stimulated with smooth LPS from *Salmonella minnesota*.

TLR2 or CD14 did not mediate GBS-induced activation of either CHO cells or human monocytes. These results are in sharp contrast to TLR2-mediated cellular activation demonstrated in response to HKLM and other Gram-positive organisms, such as *Staphylococcus aureus* and *Streptococcus pneumoniae* (Yoshimura et al., supra).

By use of blocking mabs to TLR2 and CD14, we demonstrated that HKLM cooperatively used CD14 and TLR2 to induce TNF-production from human monocytes. HKLM differ from GBS in cellular composition. Whereas group- and type-specific polysaccharides cover the encapsulated GBS-surface, it has been proposed that HKLM adhere to mammalian cells by proteins called internalins and/or by LTA (Kuhn, M. and W. Goebel. (1998), *Trends Microbiol.* 6:11–15). Antibodies against CD14 may inhibit the subsequent interaction of LTA on HKLM with TLR2 on the monocytes. The results that expression of CD14 on CHO-cells was insufficient to signal cell activation by HKLM, could be due to the inability of TLR2 to induce cell activation in these cells. The possibility exists that CD14, which also contains extracellular LRRs, interacts with TLR2 LRRs to mediate HKLM signaling.

Both HKLM- and LPS-induced activation of CHO-TLR2 cells was inhibited by the TLR2 mAb, TL2.1. In contrast to this, TL2.1 failed to inhibit LPS-induced TNF-production from human monocytes. LPS-activation through TLR2 has mostly been studied in transfected cell lines (Kirschning et al., (1998), supra) and our results indicate that this is not necessarily the main pathway of LPS-induced TNF production in monocytes.

Thus we have shown that TLR2 mediates cell activation induced by HKLM, but not by GBS suggesting that human TLR2 distinguishes between two Gram-positive pathogens.

HKLM, but not GBS, showed a time- and dose-dependent activation of Chinese hamster ovary (CHO) cells transfected with human TLR2, as measured by translocation of NFκB and induction of IL-6 production. The TLR2 mAb (TL2.1) which we generated was capable of eliminating IL-6 production from CHO-TLR2 cells stimulated with HKLM or LPS. The TL2.1 mAb inhibited HKLM-induced TNF-production from human monocytes by 60%, whereas a CD14 mAb (3C10) reduced the TNF-production by 30%. However, co-administrating TLR2 and CD14 mAbs inhibited the TNF-response by 80%. In contrast to this, anti-CD14 blocked LPS-induced TNF-production from monocytes, while anti-TLR2 showed no inhibition. Neither TLR2 nor CD14 mAbs affected GBS-induced TNF-production. These results show that TLR2 can function as a signaling receptor for HKLM, possibly together with CD14, but that TLR2 is unlikely to be involved in cell activation by GBS. Furthermore, while LPS can activate cells through TLR2, this receptor does not seem to be the main inducer of LPS-activation of human monocytes. Thus, our data demonstrate the ability of TLR2 to distinguish between different pathogens.

EXAMPLE 2

Toll-Like Receptor 2 Functions as a Pattern Recognition Receptor for Diverse Bacterial Cell Wall Products The Experiments described in this Example show that a vareity of membrane lipoproteins/lipopeptides from *Borrelia burgdorferi*, *Treponema pallidum* and *Mycoplasma fermentans* activate cells heterologously expressing TLR2, but not TLR1 or TLR4. These TLR2-expressing cells are also stimulated by living motile *B. burgdorferi*, suggesting that TLR2 recognition of lipoproteins is relevant to natural *Borrelia* infection. Importantly, a TLR2 antibody (Mab TL2.1—see Example 1) inhibited bacterial lipoprotein/lipopeptide induced tumor necrosis factor (TNF) release from human peripheral blood mononuclear cells, and TLR2-null Chinese hamster macrophages were insensitive to lipoprotein/lipopeptide challenge. The data suggest a role for the native protein in cellular activation by these ligands. In addition, TLR2-dependent responses were seen using whole *Mycobacterium avium* and *Staphylococcus aureus*, demonstrating that this receptor can function as a signal transducer for a wide spectrum of bacterial products. We conclude that diverse pathogens activate cells through TLR2 and propose that this molecule is a central pattern recognition receptor in host immune responses to microbial invasion.

Materials and Methods

Reagents

PBS, Ham's F-12 medium, RPMI 1640 and trypsin-versene mixture (trypsin-EDTA) were from BioWhittaker (Walkersville, Md.). Low endotoxin FBS was from Summit Biotechnologies (Greeley, Colo.), and ciprofloxacin was a gift from Miles Pharmaceuticals (West Haven Conn.). Hygromycin B was purchased from Calbiochem (San Diego, Calif.) puromycin from Sigma (St. Lois, Mo.), and G418 from Gibco BRL (Gaitersburg, Md.). Protein-free LPS from *Salmonella* minnesota Re595 was a gift from N. Qureshi (Middleton VA Hospital, Madison, Wis.). Antibodies for flow cytometry were purchased from Becton Dickinson, and human IL-1β and tumor necrosis factor α (TNF) were from Genzyme (Cambridge, Mass.).

Lipoproteins and Lipopeptides

Native OspA (nOspA) was immunoaffinity purified from *B. burgdorferi* strain TII-EV (Norgard et al., (1996), *Infect. Immun.* 64: 3845–3852). Hexapeptides similar to the N-termini of *B. burgdorferi* OspA (CKQNVS)), OspC (CNNSGK) and *T. pallidum* 47-kDa major lipoprotein (CGSSHH) were synthesized on an Applied Biosystems (Foster City, Calif.) peptide synthesizer. Lipopeptides (OspAL, OspCL, 47L) corresponding to the acylated N-termini of natural OspA, OspC and 47-kDa lipoprotein were synthesized using tripalmitoyl-S-glyceryl-cysteine in a solid-phase procedure (DeOgny et al., (1994), *Pept.Res.* 7:91–97). A synthetic(s) lipopeptide based upon the full length MALP-2 membrane lipopeptide from *Mycoplasma fermentans* (sMALP-2; CGNNDESNISFKEK) was prepared using dipalmitoyl-S-glyceryl cysteine as described (Garcia et al., (1998), 273: 34391–34398). An unlipidated version of sMALP-2 was also synthesized (Garcia et al., (1998), supra). Lipoproteins and lipopeptides were frozen at –20° C. as 1 mg/ml or 200 μM (sMALP-2) stock solutions in PBS (OspAL, OspCL, 47L) or in PBS/25 mM octyl glucoside (nOspA, sMALP-2). Endotoxin-levels were undetectable in all lipoprotein/lipopeptide stock solutions as measured by *Limulus* assay.

Bacterial Strains

*B. burgdorferi* strain B31 [(Fraser et al., (1997), *Nature* 390: 580–586), provided by R. Lathigra, MedImmune, Inc., Gaithersburg, Md.] was grown in vitro at 34° C. in Barbour-Stoenner-Kelly-H medium (Sigma). Microorganisms were quantified by dark-field microscopy. Spirochetes were passaged five times or less prior to experimentation, and infectivity was assessed by intradermal infection of C3H/HeJ mice (Jackson Laboratories, Bar Harbour, Me.), followed by culture of an ear biopsy. For flow cytometry experiments, *B. burgdorferi* were labeled with PKH2 green fluorescent dye (Sigma) according to the manufacturer's instructions. *Mycobacterium avium* strain 969 A45, originally a clinical isolate, was grown in Middlebrook 7H9 medium with OADC supplementation (Baltimore Biological Laboratories, Baltimore, Md.). The bacterial cells were harvested by centrifugation, washed twice and resuspended in PBS, passed through a 5 μm filter to remove cell clumps, and enumerated by plating. Heat-killed *Staphylococcus aureus* (ATCC 25923) was prepared as described (Yoshimura et al., (1999), *J. Immunol.* 163: 1–5). Bioparticles consisting of killed *Escherichia coli* K-12 strain were purchased from Molecular Probes (Eugene, Oreg.) and resuspended in PBS.

Cell Lines

The CHO/CD14.ELAM.Tac reporter cell line (clone 3E10) expresses inducible membrane CD25 under control of a region from the human E-Selectin promoter containing nuclear factor-kappa B (NF-κB) binding sites; this promoter element is absolutely dependent upon NF-κB (Delude et al., (1998), *J. Immunol* 161:3001–3009). Control reporter cells, CHO/ELAM.Tac (clone ELi) were similarly constructed to express surface CD25 upon IL-1_or TNF_stimulation by transfecting cells with the reporter construct and the hygromycin vector pCEP4 alone (i.e., without CD14). CHO/CD14 cells expressing TLRs were engineered by stable transfection of the CHO/CD14 reporter cell line with the cDNA for human TLR1, TLR2 or TLR4 in the pFLAG-CMV-1 vector [a gift from C. Kirschning and M. Rothe, Tularik Inc., South San Francisco, Calif., (Kirschning et al., (1998), *Nature* 395: 284–288)] as described (Yoshimura et al., (1999) supra). All CHO reporter cell lines were grown in Ham's F12 medium containing 10% FBS, 10 µg/ml ciprofloxacin and 400 U/ml hygromycin B. The TLR expressing cell lines contained additional selection antibiotics (for CD14/TLR2: 0.5 mg/ml G418, for CD14/TLR1 and CD14/TLR4: 50 µg/ml puromycin). A CHO/CD14 reporter cell line with defects in the LPS signaling pathway [clone 7.7, (Delute et al., (1998) supra)] was stably transfected with TLR2 or TLR4 using calcium phosphate as described elsewhere in Chen et al., 1987 *Mol. Cell. Biol.* 7: 2745–52, and grown in the presence of hygromycin and G418.

Flow Cytometry Analysis

Cells were plated at a density of 1×105/well in 24-well dishes. The following day, the cells were stimulated as indicated in Ham's F12 medium containing 10% FBS (total volume of 0.25 ml/well). Subsequently, the cells were harvested with trypsin-EDTA, and labeled with FITC anti-CD25 in PBS/1% FBS for 30 min on ice. After labeling, the cells were washed once and resuspended in PBS/1% FBS containing propidium iodide to exclude dead cells. The cells were analyzed by flow cytometry using a FACScan microfluorimeter (Becton Dickinson).

Peritoneal Macrophages

Ten week old Chinese hamsters (Cytogen Research and Development, West Roxbury, Mass.) and C3H/OuJ mice (Jackson Laboratories) were injected intraperitoneally with 2 ml of 3% thioglycollate (Sigma). After 3 days, peritoneal exudate cells were harvested by lavage with 7 ml of RPMI 1640 medium containing 10% FBS and 10 µg/ml ciprofloxacin. The cells were washed with medium, counted and plated at a density at 1.2×106/well in 6 well dishes, followed by overnight incubation. The non-adherent cells were then removed by washing with medium. Two days after harvesting, the cells were washed twice with medium and stimulated for one hour. Nuclear extracts were isolated and analyzed for binding to a [32P]-labeled NF-κB specific oligonucleotide by electrophoretic mobility shift assay, as described (Delude et al., (1994), *Proc. Natl. Acad. Sci.* 92: 9822–9292).

Isolation of PBMC and Measurement of TNF

Human peripheral blood mononuclear cells (PBMC) were isolated by gradient centrifugation of heparinized blood on Histopaque® 1077 (Sigma) according to the manufacturer's protocol. The cells were resuspended in RPMI 1640 medium containing 10% human serum and plated at a density of $7 \times 10^5$ cells/well in a 96-well dish. Immediately before stimulation with the indicated compounds, 1:5 (v/v) dilutions of a hybridoma supernatant containing the TLR2-specific antibody TL2.1 or a control antibody (mouse IgG, Sigma, diluted in hybridoma medium), to a final antibody concentration of 5 µg/ml was added. The cells were stimulated for 12 hrs, cell-free supernatants were harvested and analyzed for TNFα release by ELISA (matching antibody pair from Roche, Indianapolis, Ind.) using a procedure as described by Liabakk et al., in *J. Immunol. Methods*, 134: (1990), 253–259.

Results

TLR2, But not TLR4 or TLR1, Imparts Cellular Activation by *B. burgdorferi. T. pallidum* and *M. fermentans* Lipoproteins and Lipopeptides In order to test the potential role of TLRs in *B. burgdorferi* and *T. pallidum* infections, we constructed several TLR-expressing reporter cell lines in a CHO fibroblast background that contained an inducible NF-κB-dependent promoter driving the surface expression of membrane CD25 (Delude et al., (1998) supra). Thus, the induction of proinflammatory activity could be quantified by flow cytometry.

We exposed CHO/CD14, CHO/CD14/TLR1, CHO/CD14/TLR2 and CHO/CD14/TLR4 reporter cell lines to the purified native *B. burgdorferi* outer surface protein A (nOspA), a synthetic lipohexapeptide based upon the N-terminus of the 47 kDa major *T. pallidum* lipoprotein (47L), and a synthesized version of the sMALP-2 full length *M. fermentans* lipopeptide.

All of the cell lines were engineered to express CD14, thereby conferring responsiveness to LPS as indicated by increased membrane expression of the CD25 reporter transgene. Cells expressing TLR2 were activated by lipoprotein or lipopeptide structures (FIG. 7A).

In contrast, CHO/CD14, CHO/CD14/TLR1 and CHO/CD14/TLR4 cells were not activated by any of the spirochetal molecules. These results also illustrate an important point concerning the purity of our preparations. Lack of stimulation of the highly LPS-sensitive CHO/CD14 line is strong evidence against the possibility that environmental endotoxin contaminated our preparations.

The N-terminus of mature *B. burgdorferi* and *T. pallidum* lipoproteins consists of a diacylglyceryl moiety in thioether linkage to a cysteine residue, and a third fatty acid amide-linked to the cysteine's α-amino group (Belisle et. al., (1994), *J. Bacteriol.* 176:2151–2157). In contrast, *M. fermentans* MALP-2 possesses an N-acyl-S-diacylglceryl cysteine with a free N-terminus (Muhlradt et al., (1997), *J.Exp.Med.* 185:1951–1958).

Several reports demonstrate dependence on lipid modification for both in vivo and in vitro cellular activation by *B. burgdorferi, T. pallidum* and *M. fermentans* lipoproteins and synthetic lipopeptides (Sellati et al., (1996), *Infect. Immun.* 64: 3180–3187; Radolf et al., (1995), *J. Immunol* 154: 2866–2877; Weis et al., (1994), *Infect. Immun.* 62:4632–4636; Garcia et al., (1998) supra). As shown in FIG. 7B only lipidated peptides (*B. burgdorferi* OSpCL, OspAL, *T. pallidum* 47L and *M. fermentans* sMALP-2) activated the CHO/CD14/TLR2 reporter cell line, whereas the non-lipidated peptides completely lacked stimulatory activity.

These data demonstrate that TLR2 mediates cellular activation by lipoproteins/lipopeptides and that the N-acyl-S-diacylglceryl moiety appears to be more important than the amide/linked fatty acid for their biological activity.

The Lack of TLR4 Activity after Lipoprotein/Lipopeptide Exposure is Due to the Lack of Ligand-Specific Recognition Although the inability of the CHO/CD14/TLR4 cell line to respond to lipoproteins and lipopeptides may reflect the fact that TLR4 is not involved in lipoprotein recognition, it is possible that these cell lines expressed a nonfunctional TLR4. Control conditions were difficult to establish, because LPS already activates CHO/CD14 cells through the endogenous hamster TLR4. Therefore, an alternative approach was employed to confirm the functionality of the transfected TLR4 protein before concluding that bacterial lipoproteins and lipopeptides were not TLR4 ligands.

Our laboratory has recently described CHO/CD14 cells with a genetic defect in LPS, but not in IL-1- or TNF-induced signal transduction (Delude et al., (1998) supra). These cells respond to LPS after transfection with TLR2 or TLR4, as these Toll proteins bypass their genetic lesion[4]. As shown in FIG. 8, transfection with TLR2 enabled the cells to respond to lipopeptides, lipoproteins and LPS.

In stark contrast, TLR4-transfected cells responded to LPS only, demonstrating that the transfected TLR4 is functional in CHO/CD14 cells, but will not transduce a signal in response to lipoproteins/lipopeptides. These data suggest that TLR2 is able to serve as a receptor for a broad repertoire of bacterially derived ligands, while TLR4 appears to be a more specific receptor for LPS.

TLR2 Mediates Cellular Responses Upon Exposure to Live B. burgdorferi

Similar to spirochetal lipoproteins/lipopeptides, live B. burgdorferi and T. pallidum activated monocytic cells, but failed to stimulate CHO/CD14 cells (Sellati et. al., (1999), J. Immunol In press). These findings are one of several pieces of evidence supporting the hypothesis that live spirochetes and their constituent lipoproteins activate cells by similar, if not identical, mechanisms. In light of these results and the above observations it was of interest to test whether motile spirochetes signal through TLR2.

We found that only TLR2-transfected cells were activated upon exposure to B. burgdorferi (FIG. 9A), while CHO/CD14/TLR4 cells remained insensitive to spirochetal challenge (data not shown). Experiments with FITC-labeled B. burgdorferi showed a similar high degree of binding of the spirochete to all cell lines (data not shown), indicating that membrane attachment was not sufficient to initiate cellular responses.

Again, motile B. burgdorferi stimulated the TLR2-transfected LPS non-responder mutant CHO/CD14 cells, while TLR4-transfected cells were enabled to respond to LPS, but no to the spirochetes (FIG. 9B). Thus, the recognition of lipopeptides and lipoproteins by TLR2 appears to be relevant to the responses observed during natural infection in man. These results demonstrate that TLR2 but not TLR4 mediates responses to whole B. burgdorferi, and that TLR4 is unlikely to be involved in responses to spirochetes.

TLR2 is a Pattern Recognition Receptor

Many microbial infections induce similar clinical symptoms, which may reflect similarities in host responses to invasion. Recent observations suggest that bacterial cell wall structures such as peptidoglycan from Gram-positive organisms (Yoshimura et al., (1999) supra; Schwandner et al., (1999), J. Biol. Chem. 274: 17406–17409) are able to signal through TLR2.

M. avium is an opportunistic pathogen which leads to serious complications in HIV-1 disease; patients with M. avium experience profound fevers, diffuse pains and generalized wasting (Burman et al., (1996)). Recent observations suggest that structures from M. avium activate the LPS signaling pathway by utilizing CD14 (Lien et al., (1998), Blood 92: 2084–2092).

We exposed the transfected fibroblasts to live M. avium, and killed S. aureus and Escherichia coli, in order to determine if there were similarities in utilization of TLR2 by bacteria containing different membrane constituents.

The patterns of response demonstrated the following (FIG. 10): CHO cells required expression of CD14 in order to respond to Gram-negative cell wall products. However, cells that co-expressed CD14 with TLR2 were capable of responding respond to stimuli by all the bacteria tested, including the atypical mycobacterium M. avium and the Gram-positive bacterium S. aureus.

Hence, although they are phylogenetically diverse and contain a variety of proinflammatory constituents, M. avium, S. aureus, B. burgdorferi, T. pallidum and M. fermentan all appear to activate cells through the same receptor system, involving TLR2.

TLR2-Null Chinese Hamster Macrophages Fail to Respond to Lipoproteins/Lipopeptides Chinese hamster macrophages respond to LPS, although they do not express mRNA for a full length TLR2 (Heine et al., (1999), J. Immunol., 162: 6971–6975). Sequence analysis of TLR2 from the Chinese hamster, compared to human and mouse TLR2, revealed a single base pair deletion that resulted in a frame shift mutation; this mutation encodes for a protein fragment devoid of transmembrane and intracellular domains. In contrast, CHO/CD14 cells and macrophages from Chinese hamsters appear to have a full length and functional TLR4.

We isolated peritoneal macrophages from Chinese hamsters in order to test the action of lipoproteins/lipopeptides towards TLR2-null primary phagocytes. We found that the hamster macrophages responded to LPS, but not to nOspA or 47L, as measured by nuclear translocation of NF-κB (FIG. 11A). In contrast, macrophages from C3H/OuJ mice responded to both LPS, nOspA and 47L.

These results suggested that the lack of TLR2 in primary Chinese hamster macrophages made them unable to recognize bacterial lipoproteins and lipopeptides.

The Anti-TLR2 mAb TL2.1 Inhibits Lipoprotein/Lipopeptide and M. avium Induced Release of TNF from Human Peripheral Blood Mononuclear Cells In order to determine if our findings in transfected cell lines reflect the signal transduction systems used by native phagocytes, we stimulated freshly isolated human PBMC with nOspA, 47L and M. avium in the presence of the TLR2 antibody TL2.1. As shown in FIG. 11B, TL2.1 inhibited TNF production from PBMC after exposure to nOspA, 47L and live M. avium by 40–70%.

These data support the hypothesis that TLR2 may play an important role in in vivo responses to various bacterial structures. In the presence of TL2.1, LPS-induced responses in primary cells were only minimally reduced (results not shown). Although the relative importance of TLR2 in LPS signaling remains unclear, expression of TLR2 (unlike TLR4) does not appear to be required for cell responses to low concentrations of LPS.

CHO/CD14 fibroblast cell lines were engineered to express TLR2. The transfected cells were highly susceptible to activation by lipoproteins and lipopeptides from B. burgdorferi, T. pallidum and M. fermentans, as well as to activation by live motile B. burgdorferi. In contrast, cells expressing TLR1 or TLR4 did not acquire responsiveness to bacterial lipoproteins/lipopeptides. Moreover, we observed a TLR2-mediated cell activation by Mycobacterium avium, an important pathogen in AIDS.

Thus it seems that TLR2 mediates cellular responses to structures from numerous microbial cell wall constituents, and may thus be central in host recognition of diverse bacterial pathogens. Therapies directed at the TLRs may be useful anti-inflammatory agents for a large variety of chronic and acute bacterial infections.

Both TLR2 and TLR4 have been reported to function as LPS signal transducers. Our data support these conclusions, although they suggest that the two related proteins clearly have different roles in pathogen recognition: TLR4 is required for sensitive responses to LPS, while TLR2 is not. In a broad sense, the accumulated data indicates that the preferential utilization of TLRs underlies both the observed similarities, as well as the differences, in specific pathogen recognition.

Furthermore, the present data do not rule out the possibility that TLR2 may have a more important function in LPS recognition by non-phagocytic cells.

EXAMPLE 3

Studies on Antibody TL2.1—Specificities and Properties

1. Binding Specificity

Properties of the TL2.1 Monoclonal Antibody

The specificity of the TL2.1 monoclonal antibody is demonstrated in Table 1 (binding data with flow cytometry) and FIG. 4 (immunoprecipitation of labelled CHO-TLR lysate).

Table 1—Summary of Binding Specificity of TL2.1

The following table summarises the binding characteristics of TL2.1. These binding experiments on cells have been performed with fluorochrome labelled (Alexa 488) TL2.1 antibody and analysed with a Flow cytometer.

| Cells | TL2.1 |
|---|---|
| CHO-neo | Negative |
| CHO-TLR2 | Positive |
| CHO-CD14/TLR4 | Negative |
| Human NK cells (CD56+) | Negative |
| Human B-cells (CD19+) | Negative |
| Human neutrophils (CD15+, weakly CD14+) | Positive |
| PBMC | Positive (only the CD14+ cells) |
| Mono-Mac 6 (hu. monocyte cell line, CD14+) | Positive |
| U-937 (hu. monocyte cell line, CD14 negative) | Positive |
| U-373 neo (human astrocytoma) | Negative |
| U-373 CD14 | Negative |
| EaHy (human endothelial cell line) | Negative |
| SW 480 (human adenocarcinoma) | Negative |
| HMEC-1 (human endothelial cell line) | Negative |
| 70Z/3-CD14 (murine B-cell line transfected with CD14) | Negative |
| RAW (murine macrophage cell line) | Positive |

In addition to these specificity controls, Western blotting cell lysates was formed from CHO-neo, CHO-TLR4 and CHO-TLR2 cells was performed. Since the CHO cells are transfected with a FLAG-TLR2 construct TLR2 can also be detected with a FLAG antibody in this system. The results shown in FIG. 12 show that TL2.1 and FLAG antibodies detect a protein with the same molecular weight. Based on these results and taken together with the results shown in FIG. 4, it is concluded that it is very likely that TL2.1 detects an epitope on the human TLR2 molecule.

A number of human B-cell lines were tested for binding of TL2.1 and were found to be negative. These cell lines are: Daudi, RPMI8226, U-266, JJN-3 and Saos-2. A unique property of TL2.1 is the binding to murine macrophages. This is shown in FIG. 13. This indicates that TL2.1 cross-reacts with both human and murine TLR2. Results we have with TL2.1 suggest that it does not bind to CD14+TLR2- human PBMCs.

2. Functional Effects of TL2.1

Two strains *M. Tuberculosis* (H37Rv) and Ra were added to murine macrophages isolated from the peritoneal cavity of C3H/HeJ mice. In the experiment shown in FIG. 14, anti TLR2 (TL2.1) and a control antibody (both at 10 ug/ml) were added together with the pathogens. Production of tumour necrosis factor (TNF) from the macrophage cultures was measured by an ELISA assay using a commercial kit purchased from R&D Systems. As can be seen from FIG. 14, the TL2.1 inhibits the TNF production, whereas the control antibody has no effect.

The results displayed in FIG. 15 show that the mannuronic acid polymer (poly M) has an epitope that interacts with TLR2 and that this epitope is important for the cytokine stimulating ability of this polymer. In particular, FIG. 15 shows that TL2.1 inhibits TNF production from human monocytes stimulated with poly M. This statement is further supported by data showing that this polymer will inhibit (reduce) binding of the TL2.1 antibody to human monocyte cells isolated from blood cells, (FIG. 16B) but does not inhibit binding of an irrelevant mouse antibody used as control (FIG. 16A). To generate this data the cells (PBMC) were preincubated with the polymer (poly M) (2000 µg/ml) for 1 hour on ice before 25 µg/ml Alexa 488 labelled TL2.1 was added and incubated for an additional 1 hour on ice. The samples were then run on a FacsScan flow cytometer, with 5000 cells in each histogram (FIG. 16B). In FIG. 16A, the controls with an irrelevant mouse antibody are shown.

3. Use of the TL2.1 MAB for Histology Examination

Expression of TL2.1 in human tissue has also been examined by the TL2.1 antibody. Freeze sections were made from tonsil tissue, which were incubated with the TLR2 antibody. Microscopic examination of the sections revealed that TLR2 was expressed only on a limited number of cells (FIG. 16), which resembles tissue macrophages. Also, some cells around vascular like structures are positive. The nature of these cells are not known. These results demonstrate that the TL2.1 recognises cells in a specific manner in human lymphoid tissue.

What is claimed is:

1. An isolated antibody that binds to human TLR2 and which
   (i) binds only to CD14$^+$ cells in a normal human mononuclear cell population, and not to CD14$^-$ cells;
   (ii) does not inhibit LPS-induced activation of normal human mononuclear cells.

2. An antibody as claimed in claim 1 wherein said antibody does not bind to TLRs of other classes.

3. An antibody as claimed in claim 1 wherein said antibody does not bind to TLR4.

4. An antibody as claimed in claim 1 wherein said antibody does not inhibit LPS-induced TNF release by normal human mononuclear cells.

5. An antibody as claimed in claim 1, wherein said antibody inhibits lipoprotein or lipopeptide-induced activation of normal human mononuclear cells.

6. An antibody as claimed in claim 1 that cross-reacts with murine TLR2.

7. An antibody as claimed in claim 6 which is a murine antibody that binds specifically to hTLR2 and to mTLR2.

8. An antibody as claimed in claim 1, wherein the binding of said antibody to normal human mononuclear cells is inhibitable by mannuronic acid polymers.

9. An antibody as claimed in claim 1 that binds specifically to TLR2$^+$ cells.

10. An antibody as claimed in claim 1 that inhibits the effect of human alveolar macrophages in killing *Cryptococcus*.

11. An antibody as claimed in claim 1 which is of a single specificity.

12. An antibody as claimed in claim 1 which is (i) chosen from the group consisting of IgG, IgA, IgM, IgD and IgE; or (ii) a monoclonal or polyclonal antibody; or (iii) an antibody fragment; or (iv) synthetic.

13. A hybridoma or cell-line producing an antibody as claimed in claim 1.

14. An isolated monoclonal antibody (designated as TL2.1) produced by the hybridoma cell line of European Collection of Cell Cultures (ECACC) deposit Accession No. 99102832.

15. An isolated antibody having the same binding specificities as antibody TL2.1 produced by the hybridoma of ECACC Accession No. 99102832.

16. An antibody as claimed in claim 1, wherein said antibody carries or is provided with a label, or is immobilized or bound to a carrier.

17. A hybridoma or cell line being that on deposit at the ECACC under Accession No. 99102832, or producing an antibody having the binding specificities of monoclonal antibody TL2.1 produced by the hybridoma of ECACC accession No. 99102832.

18. A method of making the antibody of claim 1, comprising the steps of:

a) immunizing a host animal with a TLR2 immunogen;

bi) generating a polyclonal antibody; or bii) generating a monoclonal antibody;

c) recovering said antibody.

19. A method of treatment of a bacterial infection in a patient in need thereof, said method comprising administering to said patient an antibody as defined in claim 1.

20. A pharmaceutical composition comprising an antibody as defined in claim 1 together with at least one pharmaceutically acceptable carrier or diluent.

21. A method of detecting TLR2 in a sample which comprises contacting said sample with an antibody as defined in claim 1, and determining whether there is binding to the sample.

22. The method of claim 19 wherein the bacterial infection is a *Listeria* infection.

23. A method of treatment of *Listeria* infection in a patient in need thereof, said method comprising administering to said patient an agent that inhibits TLR2 activation, wherein said agent is an anti-TLR2 antibody.

24. A method of inhibiting TLR2 activation in a patient in need of such inhibition, said method comprising administering to said patient an antibody that binds to human TLR2 and that (i) binds to $CD14^+$ cells in a normal human mononuclear cell population, and not to $CD14^-$; and (ii) does not inhibit LPS-induced activation of normal human polynuclear cells.

* * * * *